United States Patent [19]

Vestal et al.

[11] Patent Number: 4,960,992

[45] Date of Patent: * Oct. 2, 1990

[54] METHOD AND MEANS FOR VAPORIZING LIQUIDS BY MEANS OF HEATING A SAMPLE CAPILLARY TUBE FOR DETECTION OR ANALYSIS

[75] Inventors: Marvin L. Vestal, Houston; Calvin R. Blakely, Kingwood, both of Tex.; Gordon J. Fergusson, Claremont, Calif.

[73] Assignee: Research Corporation Technologies, Tucson, Ariz.

[*] Notice: The portion of the term of this patent subsequent to Mar. 21, 2006 has been disclaimed.

[21] Appl. No.: 326,150

[22] Filed: Mar. 20, 1989

Related U.S. Application Data

[63] Continuation of Ser. No. 31,150, Mar. 25, 1987, which is a continuation of Ser. No. 687,719, Dec. 31, 1984, abandoned, which is a continuation-in-part of Ser. No. 527,751, Aug. 30, 1983, abandoned.

[51] Int. Cl.$^5$ ............................................. H01V 49/28
[52] U.S. Cl. ................................ 250/288; 73/863.12; 73/864.81
[58] Field of Search ............. 250/281, 282, 288, 423 R; 422/70; 436/161; 73/61.1 C, 863.12, 863.21, 864.81

[56] References Cited

U.S. PATENT DOCUMENTS

| | | | |
|---|---|---|---|
| 2,712,073 | 6/1955 | Martin | 250/41.9 |
| 2,715,273 | 8/1955 | Hull et al. | 250/41.9 |
| 2,717,962 | 9/1955 | Wouters | 250/425 |
| 2,727,151 | 12/1955 | Parkins | 250/41.9 |
| 2,789,229 | 4/1957 | Lawrence | 250/41.9 |
| 2,824,967 | 2/1958 | Kamen | 250/41.9 |
| 2,978,580 | 4/1961 | Von Ardene | 250/41.9 |
| 3,229,409 | 1/1966 | Johnson | 43/129 |
| 3,449,563 | 6/1969 | Brown | 250/41.9 |
| 3,458,699 | 7/1969 | Padrta | 250/41.9 |
| 3,560,627 | 2/1971 | Langer | 13/31 |
| 3,697,748 | 10/1972 | Cohen | 250/281 |

(List continued on next page.)

OTHER PUBLICATIONS

Studies of Ionization Mechanisms Involved in Thermospray LC-MS, Vestal, Int. J. Mass Spectrom. Ion Phys. 51 (1983) pp. 193-196.

(List continued on next page.)

Primary Examiner—Jack I. Berman
Attorney, Agent, or Firm—Scully, Scott, Murphy & Presser

[57] ABSTRACT

This disclosure is concerned with method and apparatus for vaporizing liquid solutions in order to detect, quantitate, and/or determine physical or chemical properties of samples present in liquid solution. Mixtures may be separated by an on-line liquid chromatographic column and the methods used for detection, quantitation, identification, and/or determination of chemical and physical properties include mass spectrometry, photoionization, flame ionization, electron capture, optical photometry, including UV, visible, and IR regions of the spectrum, light scattering, light emission, atomic absorption, and any other technique suitable for detecting or analyzing molecules or particles in a gaseous or vacuum environment. The method and apparatus involves controlled partial vaporization of the solution. Methods are disclosed for controlling the degree of partial vaporization and the temperature at which this vaporization occurs, and for maintaining this degree of vaporization essentially constant even though the solvent flow rate and/or composition may vary in either a controlled or an uncontrolled fashion. This "thermospray" method and apparatus allows the solvent to be substantially vaporized to produce a supersonic free jet containing a fraction of unvaporized solvent as liquid droplets entrained in the jet. Solutes which are less volatile than the solvent are preferentially contained in the droplets. Methods are disclosed for controlling the temperature at which the process occurs in order to prevent unwanted chemical modification of the solutes (for example, pyrolysis) and to prevent premature vaporization of the solutes.

21 Claims, 20 Drawing Sheets

U.S. PATENT DOCUMENTS

| | | | |
|---|---|---|---|
| 3,751,660 | 8/1973 | Thurston | 250/41.9 |
| 3,801,788 | 4/1974 | Milne | 250/41.9 ME |
| 3,851,146 | 11/1974 | Bennett | 219/300 |
| 3,888,107 | 6/1975 | Langer et al. | 73/15 B |
| 3,896,661 | 7/1975 | Parkhurst et al. | 73/61.1 C |
| 3,943,363 | 3/1975 | Amblard | 250/288 |
| 3,997,298 | 12/1975 | McLafferty et al. | 23/253 R |
| 4,024,217 | 5/1977 | Wexler et al. | 423/19 |
| 4,055,987 | 11/1977 | McFadden | 73/61.1 C |
| 4,066,409 | 1/1978 | Fine | 23/230 PC |
| 4,112,297 | 9/1978 | Miyagi et al. | 250/288 |
| 4,122,343 | 10/1978 | Risby et al. | 250/282 |
| 4,140,905 | 2/1979 | Polanyi | 250/281 |
| 4,156,814 | 5/1979 | Hunt et al. | 250/423 P |
| 4,160,161 | 7/1979 | Horton | 250/281 |
| 4,178,507 | 12/1979 | Brunnee et al. | 250/282 |
| 4,197,455 | 4/1980 | Blanchard et al. | 250/288 |
| 4,209,696 | 6/1980 | Fite | 250/281 |
| 4,239,967 | 12/1980 | Carr et al. | 250/281 |
| 4,281,246 | 7/1981 | White et al. | 250/282 |
| 4,298,795 | 11/1981 | Takeuchi et al. | 250/282 |
| 4,300,044 | 11/1981 | Iribarne et al. | 250/282 |
| 4,403,147 | 9/1983 | Melera et al. | 250/288 |
| 4,531,056 | 7/1985 | Labowsky et al. | 250/288 |
| 4,590,371 | 5/1986 | Ottley | 250/284 |
| 4,647,772 | 3/1987 | Lewis et al. | 250/288 |
| 4,814,612 | 3/1989 | Vestal et al. | 250/288 |

OTHER PUBLICATIONS

Design and Performance of a Simplified LC-MS Using the Thermospray Technique, Blakely et al., 1982.

Ion Emissions from Liquids, Vestal.

Vestec Corporation, Thermospray LC-MS Kits and Interfaces, the first sale of applicants device.

Amino Acids Sequence of Polypeptides by Enzymatic Hydrolysis and Direct Detection Using a Thermospray LC-MS.

Mass Spectrometry Reviews, 1983, 2 pp. 447–480 (Ionization Technique for Non-Volatile Molecules).

"LC/MS Coupling", by Arpino and Guiothon Analytical Chemistry, vol. 51, No. 7, June, 1979.

"Thermospray Interface for Liquid Chromatography/Mass Spectrometry", by Blakley and Vestal, American Chemical Society, 1983.

METHOD AND MEANS FOR VAPORIZING LIQUIDS BY MEANS OF HEATING A SAMPLE CAPILLARY TUBE FOR DETECTION OR ANALYSIS

GOVERNMENT SUPPORT

The invention described herein was made in the course of work under a grant or award from the Department of Health and Human Services (formerly Health Education and Welfare).

CROSS REFERENCE TO RELATED APPLICATIONS

This is a continuation of copending application Ser. No. 031,150 filed on Mar. 25, 1987 which is a file wrapper continuation of application Ser. No. 687,719 filed Dec. 31, 1984 which is a continuation-in-part of application Ser. No. 527,751 filed Aug. 30, 1983.

FIELD OF INVENTION

The present invention relates to the field of analytical chemistry and process flow control, and is particularly adapted to vaporize the eluent from a liquid chromatograph so that samples separated by liquid chromotagraphy may be detected and/or analyzed by a mass spectrometer, or other vapor phase detection system or analytical instrument. It is particularly useful for vaporizing non-volatile, ionic or thermally labile samples that need to be separated from a liquid solution without introducing unwanted chemical modification such as pyrolysis and without materially effecting the temporal distribution of the sample.

BACKGROUND OF THE INVENTION

Both analytical chemistry and, process flow control make wide use of liquid chromatographs to analyze solutions. The output of the liquid chromatograph may be applied to a mass spectrometer, or any one of a variety of vapor phase detectors such as those utilizing photoionization, electron capture or flame ionization techniques, but to do so, the solution must be vaporized. Many methods are known for vaporizing solids and liquids for use with these devices, but these techniques cannot be generally applied to the vaporization of solutions of non-volatile solutes without producing uncontrolled chemical modification of the solute, such as pyrolysis, or without causing the solute to "salt out" on solid surfaces. In addition, various techniques applicable to some types of detection and analytical chemistry cannot be applied to others because of solvent interference or matrix effects. In addition, certain large, thermally labile molecules are difficult to vaporize inasmuch as they fragment in an uncontrolled manner when subjected to excessive heat.

The need to convert materials to be analyzed or detected into an ion vapor has been a problem in the field of the analytical chemistry for which no completely satisfactory solution has heretofore existed. Gaseous compounds or compounds which can be thermally vaporized without decomposition can usually be converted to an ion vapor relatively easily by heating the compound to vaporize it if it is not a gas, and either bombarding the compound in its gaseous state with a beam of electrons (electron impact ionization) or by introducing chemically-reactive ions into the gas (chemical ionization). However, many compounds are not sufficiently volatile at ambient temperatures to form a gas suitable for either electron-impact ionization or chemical ionization, and moreover, may be decomposed when heated so that they cannot be vaporized thermally. Among the compounds which cannot be converted into an ion vapor by these conventional techniques are many which are of biological, medical and pharmaceutical interest.

A number of special techniques have been developed to generate an ion vapor from compounds of low volatility. These techniques include field desorption, plasma desorption, rapid evaporation from inert surfaces and secondary ionization mass spectrometry. In addition to these, other techniques may be found in *Analytical Chemistry*, vol. 51, pp. 682A-701A (June 1979). None of these techniques is without its limitations, however, and a need still exists for an improved method for obtaining mass spectra of involatile, heat sensitive materials.

The problems, of forming an ion vapor of involatile and heat sensitive compounds become particularly acute when it is attempted to use-a mass spectrometer to analyze the effluent of a liquid chromatograph. Liquid chromatographs are widely used to separate mixtures into the component compounds, and find particular application when one or more of the component compounds is too involatile to permit the mixture to be separated with a conventional gas chromatograph. Although mass spectrometers have been widely and successfully interfaced to gas chromatographs to permit mass spectra to be taken of compounds in gaseous effluent from the chromatograph, efforts to interface liquid chromatographs to mass spectrometers, have been less successful, in part because compounds eluted from the liquid chromatograph are frequently involatile and heat sensitive and thus not amenable to conversion into ion vapor by conventional techniques. Moreover, the compounds to be analyzed from a liquid chromatograph are dissolved in a volatile solvent, which tends to reduce the ionization efficiency of the mass spectrometer even further with respect to the solute compounds of interest since solvent vapor is generally ionized along with the solute compounds and the solvent is typically in a much greater concentration then the solute compounds.

One attempt to interface the mass spectrometer to a liquid chromatograph is described in the U.S. Pat. No. 4,160,161 to Horton. Effluent from a liquid chromatograph is injected into an ion chamber maintained at a low pressure by means of a needle which projects into the chamber. The low pressure in the chamber, pulls the solvent and solute through the needle and sprays it into the chamber. A laser or other heat source may be utilized to prevent the effluent from freezing as it flows through the needle and to provide heat to the effluent within the ion chamber. The needle is maintained at a high voltage by a high voltage power supply so that the spray carries a charge. The solvent evaporates in a low pressure environment, reducing the size of the charge droplets until ideally only the ions remain. However, the application of high voltage in the presence of gases and vapor may cause the vapor phase to break down and become electrically conductive. The resultant uncontrolled electrical discharges in the ion chamber leads to unstable and erratic behavior.

Another method and apparatus for connecting a liquid chromatograph directly to a mass spectrometer was disclosed in U.S. Pat. No. 4,298,795 to Takeuchi et al. The patent describes a process whereby the liquid effluent is nebulized in a high temperature environment of approximately 300°. The second capillary tube is utilized to draw the molecules of interest into the mass spectrometer while an off axis pump withdraws the bulk of the solute that is not drawn into the second capillary In addition, a heating means is provided for the second capillary to prevent recondensation of the effluent on the internal walls of the capillary.

Applicants invention may be distinguished from each of the above references inasmuch as the present application uses a thermal spray to partially vaporize a solution. By partially vaporizing the solution within a capillary tube, the expanding vapor phase of the solution is used to create a thermal spray of relatively dry particles in an intense vapor jet which issues from the capillary nozzle. The vaporization of the solution creates particles of solution which preferentially contain the molecules of interest to be analyzed. These particles are expelled at velocities up to and including supersonic velocity by the expanding vaporized solvent present in the capillary tube.

SUMMARY OF THE INVENTION

This invention discloses a method and apparatus for vaporizing liquid solutions in order to detect, quantitate, and/or determine physical or chemical properties of samples present in liquid solution. Mixtures may be separated by an on-line liquid chromatographic column and the methods used for detection, quantitation, identification, and/or determination of chemical and physical properties include mass spectometry, photoionization, flame ionization, electron capture, optical photometry including UV, visible and IR regions of the spectrum, light scattering, light emission, atomic absorption, and any other technique suitable for detecting or analyzing molecules or atoms in a gaseous or vacuum environment.

The novel thermospray method consists of a two-step process. The first step is controlled partial vaporization of the solution Methods are disclosed for controlling the degree of partial vaporization and the temperature at which this vaporization occurs, and for maintaining this degree of vaporization essentially constant even though the solvent flow rate and/or composition may vary in either a controlled or an uncontrolled fashion. This thermospray method allows the solvent to be substantially vaporized to produce a supersonic free jet containing a fraction of unvaporized solvent as liquid droplets entrained in an intense vapor jet. Solute molecules of interest which are less volatile than the solvent are preferentially contained in the droplets. Methods are disclosed for controlling the temperature at which this process occurs in order to prevent unwanted chemical modification of the solutes (for example, pyrolysis) and to prevent premature vaporization of the solutes.

Several different methods may be used for the second stage of the vaporization depending on the application and the characteristics of the analytical technique to be employed. Conditions may be chosen in the first stage so that the droplets or particles produced are accelerated to high velocities, in some cases exceeding the local velocity of sound. Depending on the application, these droplets or particles may be further vaporized by internal enthalpy or by environment interaction in a heated zone; they may be directed onto a relatively cool surface where the less volatile components will stick while the remainder of the solvent and any volatile components are vaporized. Alternatively, sufficient heat may be supplied in the gas phase that all of the solvent and substantially all of the solute is vaporized without coming directly in contact with any heated surface This method is particularly useful for directly coupling a liquid chromatograph with a mass spectrometer methods are disclosed for separating the sample particles and molecules of interest from some or substantially all of the solvent vapor prior to significant vaporization of the sample. A method and apparatus are disclosed for producing a high velocity beam of particles containing nonvolatile molecules which may be analyzed by techniques suitable for studying such beams in a vacuum. In some cases the samples may be analyzed as solids deposited on a surface, in others they may be revaporized in a subsequent step for analysis by a gas phase technique.

The thermospray method allows controlled vaporization of solutions in such a way that the chemical nature of solutes is not changed by the process even though they may be nonvolatile., ionic, or thermally labile. The technique was originally developed as a means of coupling liquid chromatography to mass spectrometry, but it has a variety of other potential applications. Some of these are described later in this application. While there may be other important applications, the present discussion of the invention describes its application to analytical chemistry. It is common in a number of analytical situations that the analyte is in the form of a liquid solution. In some cases (e.g. near UV and visible photometry) the solute can be detected and analyzed in solution since the properties of the solvent may be sufficiently different from those of the solute so as not to interfere with the measurement. In other cases, either because of solvent interference or because the analytical method (for example, mass spectrometry) is a gas phase technique, it is necessary to vaporize the solution. Since the solvent is usually not of direct interest and also because it may interfere in some way with the desired measurement, it is often necessary or desirable to vaporize the solution in such a way that some, or substantially all, of the solvent is separated from the solute or solutes of interest. It is also very important in many cases that the solute not be chemically modified (for example, by pyrolysis) as a result of the vaporization process. Whether or not the solvent is removed preferentially, it is important that the solute be efficiently transferred to the analytical instrument if high sensitivity is to be achieved. Up to now there has been no practical way of accomplishing the desired performance, particularly when the sample is a non-volatile and/or thermally labile substance in an aqueous solution. The thermospray technique is particularly well-suited for these most demanding applications, and also provides a simple, economical, and efficient vaporization technique for many less difficult applications.

The thermospray system begins with the vaporizer and its associated control system. This device provides controlled partial vaporization of liquid streams containing solutes which may be nonvolatile, ionic, and/or thermally labile. A supersonic jet of vapor is produced which contains entrained liquid droplets and/or solid particles. Samples whose volatility is less than that of the solvent are preferentially contained in these droplets or particles. Method and apparatus are disclosed both for accomplishing the desired degree of vaporization of the liquid stream and for controlling the vaporizer so that this desired degree of partial vaporization is achieved even though the solvent composition or flow rate may vary.

In some cases the thermospray vaporizer may be combined directly with well-known analytical techniques to achieve useful results, but in others it is necessary to provide additional control over the temperature and pressure of the environment surrounding the supersonic jet and downstream of the Mach disk to achieve the desired results. This downstream control system is particularly important in the application to direct LC-MS coupling both for analysis of neutral molecules and for direct controlled vaporization of molecular ions from electrically charged droplets and particles. Details of the individual components and combinations into complete systems for various applications will be hereinafter described in detail.

The thermospray vaporizer uses a small diameter capillary tube through which liquid is forced at essentially constant flow rate, for example, by the kinds of pumps typically used in high pressure liquid chromatography. Depending on the application, the end of this tube may be in gas (for example air) at atmospheric pressure (or higher) or may be in a substantially reduced pressure environment. To produce the thermospray jet it is necessary to heat the tube sufficiently to produce the desired degree of vaporization. In earlier experiments, some vaporization was produced by heating the end of the tube with a $CO_2$ laser or with an oxy-hydrogen flame. Neither of these techniques was entirely satisfactory since they were difficult to control and required that the tube be heated in a rather small region to rather high temperatures to achieve the required heat input. More recently, an electrically heated vaporizer was created for this purpose but it was also only partially satisfactory.

The present invention solves the previous problems and provides satisfactory definition and control of the parameters of the vaporizer required to achieve specific results. The invention includes a control system that maintains a desired degree of partial vaporization even though the solvent composition and flow rate may vary in either a controlled or an uncontrolled manner.

The present invention uses two means for supplying the necessary heat to the flowing liquid. One means employs commercial cartridge heaters embedded in a block of material with high thermal conductivity such as copper, which is in intimate thermal contact with the tube. Such thermal contact can be achieved, for example, by silver brazing the tube to the copper block The second means employs direct ohmic heating of the tube by passing an electrical current through the tube. The first method has the advantage of providing a very stable input of large amounts of heat without introducing any uncontrolled regions of high temperature in contact with the fluid The disadvantage of the first method is that the thermal mass may make its time response too slow to cope properly with rapid composition or flow changes which sometimes occur. The second method provides a very rapid and efficient method for transferring heat into the flowing liquid. The disadvantage is that the local temperature depends very strongly on the contact with the liquid, and when operated at high degrees of partial vaporization, thermal contact with the fluid may become poor at the nozzle end. As a result the temperature at the nozzle may become such that the "leidenfrost" phenomenon occurs which effectively prevents further contact in this region. This can result in a runaway excursion of the temperature near the end of the tube. The electrical connection at the nozzle end of the tube can also introduce an undesirable pertubation of the temperature profile in the capillary Care must be taken to insure that the tube is heated uniformly right up to the exit. Ideally, the electrical connection should be of low thermal mass, and any length of unheated capillary at the nozzle end must be minimized.

Either of these techniques can provide satisfactory performance for some applications, particularly if either the flow rate or the composition of the liquid is essentially constant. Satisfactory performance can be achieved merely by controlling the power input at the proper level to produce the desired degree of vaporization. This may be accomplished by sensing the heater power directly or by sensing the temperature of the copper block or the tube itself and controlling the heat input so as to maintain this temperature constant.

When using the copper block vaporizer, better control of the vaporizer can be achieved by sensing the downstream temperature of the jet. The location of the probe in the jet is not particularly critical since the absolute temperature indicated can be correlated with the desired degree of partial vaporization in separate calibration measurements. To avoid disruption of the free jet expansion it is generally required that this probe be located off the jet axis and downstream of the Mach disk. The power input to the copper block heaters is controlled to maintain the temperature constant at the downstream temperature sensor using a standard proportioning controller. This method of controlling the vaporizer provides satisfactory correction for slow variations in solvent flow rate and composition.

A similar approach can also be applied to the vaporizer using direct ohmic heating of the capillary tube, but somewhat better performance is obtained using a temperature sensor attached to the capillary. In this case it is desirable that the sensor be located somewhere along the first one-third of the heated portion of the capillary as measured from the end corresponding to the liquid input. Typically, this sensor is placed at a point one-fourth to one-sixth of the total heated length from the liquid entrance. This location of the temperature sensor assures that the fluid inside the capillary is still entirely in the liquid state at this point and the temperature at the outer surface of the capillary is a good representation of the temperature of the liquid. By controlling the power applied to the capillary so as to maintain this temperature constant, the desired degree of vaporization may be maintained essentially constant even though the liquid flow rate may vary in either a controlled or an uncontrolled manner. Furthermore, the response of this system may be sufficiently fast to allow automatic compensation for the rapid flow fluctuations which are sometimes introduced by liquid chromatographic pumping systems.

Alternatively, a combination of the two types of vaporizers may be used. These can be combined in either order, but we have found the most effective combination to be the use of the directly heated capillary vaporizer at the inlet side and the indirectly heated block vaporizer at the vaporizer exit. The downstream jet temperature or the copper block temperature may be used to control the power input to the block heater and the temperature of the capillary in the region where vaporization has not yet begun can be used to control the heater power input to the capillary heater. This combination has several important advantages over either alone. Slow variations in liquid flow rate or composition can be compensated for with the block heater controlled by the downstream temperature sensor while rapid flow fluctuations can be compensated by the fast response directly heated vaporizer. The downstream temperature sensor may also be used to control heat to both vaporizers; in this case both power supplies can be controlled from a single temperature controller. The temperature sensor attached to the capillary tube can also be, used to control both power supplies.

In additions to requiring that the desired degree of vaporization be achieved in the thermospray vaporizer, most applications require that the temperature and pressure of the vapor surrounding the thermospray jet be controlled so that vaporization rates of the droplets carried in the jet are in the appropriate range for the particular application. The requirements for this control of the downstream environment depend strongly on what ultimate fate of the droplets or particles is desirable for a particular application. For example, in direct coupling of a liquid chromatograph to a mass spectrometer using the thermospray method, it is desirable to completely vaporize the solvent and the solutes by the time the particles reach the ion sampling aperture of the mass spectrometer, while in using thermospray to deposit nonvolatile sample on a surface it is desirable to vaporize most of the solvent from the particles before they strike the surface but none of the solute.

DETAILED DESCRIPTION OF THE PREFERRED EMBODIMENTS

Figure 1:
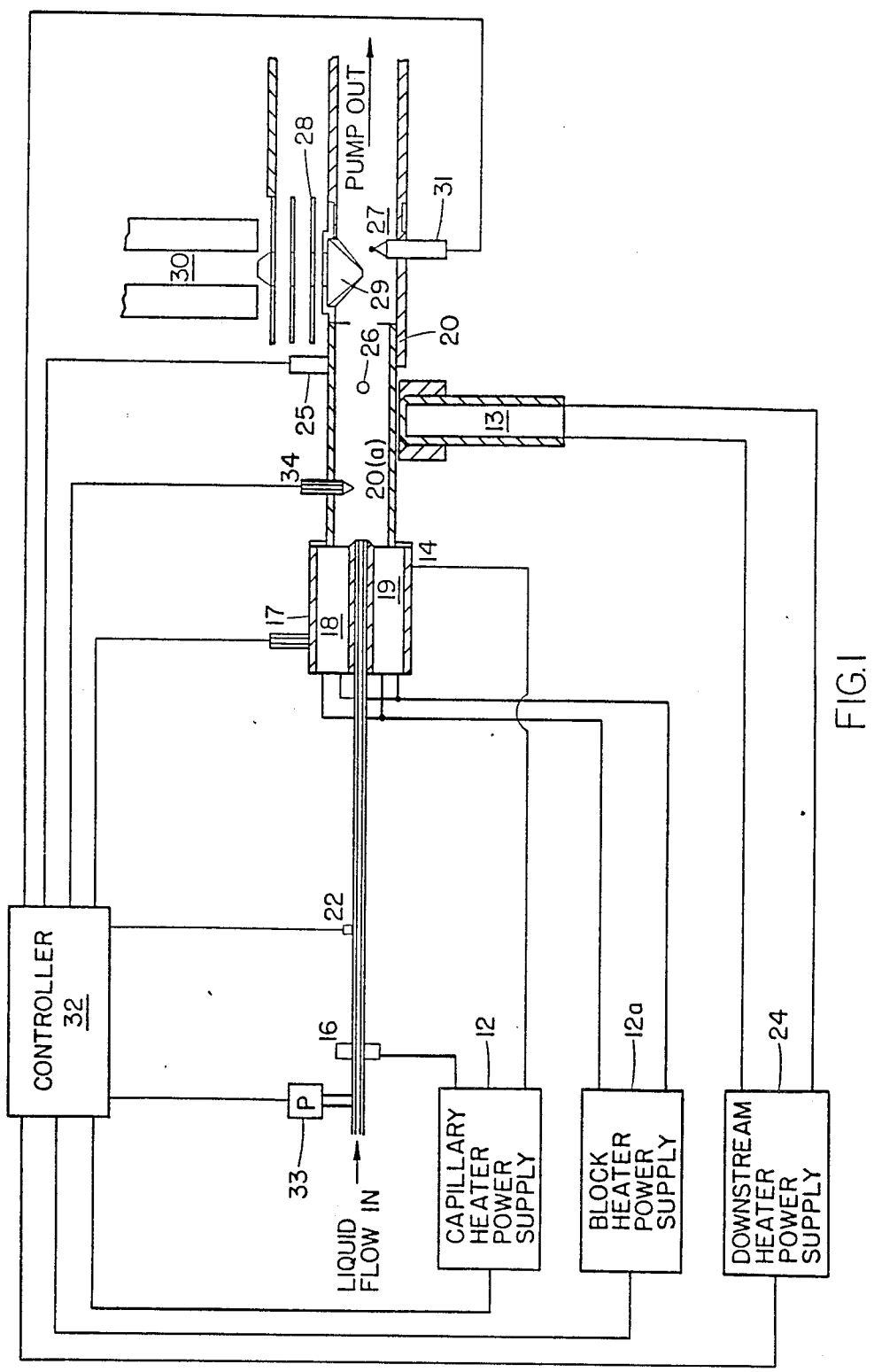
FIG. 1 is a diagrammatic and partially cross-sectioned view of a thermospray apparatus constructed in accordance with teachings of the present invention.
Figure 2:
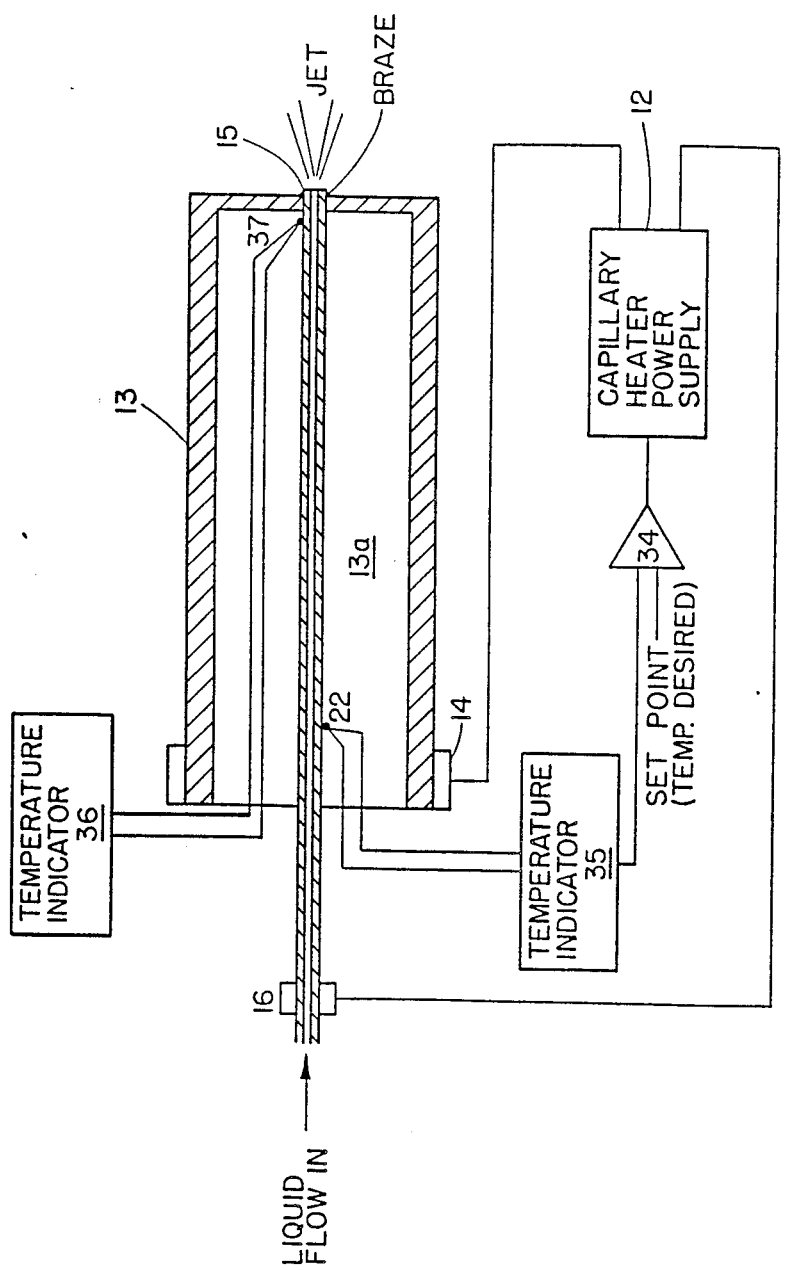
FIG. 2 is a diagrammatic and partially cross-sectioned view of an alternate embodiment of the present invention.
Figure 3:
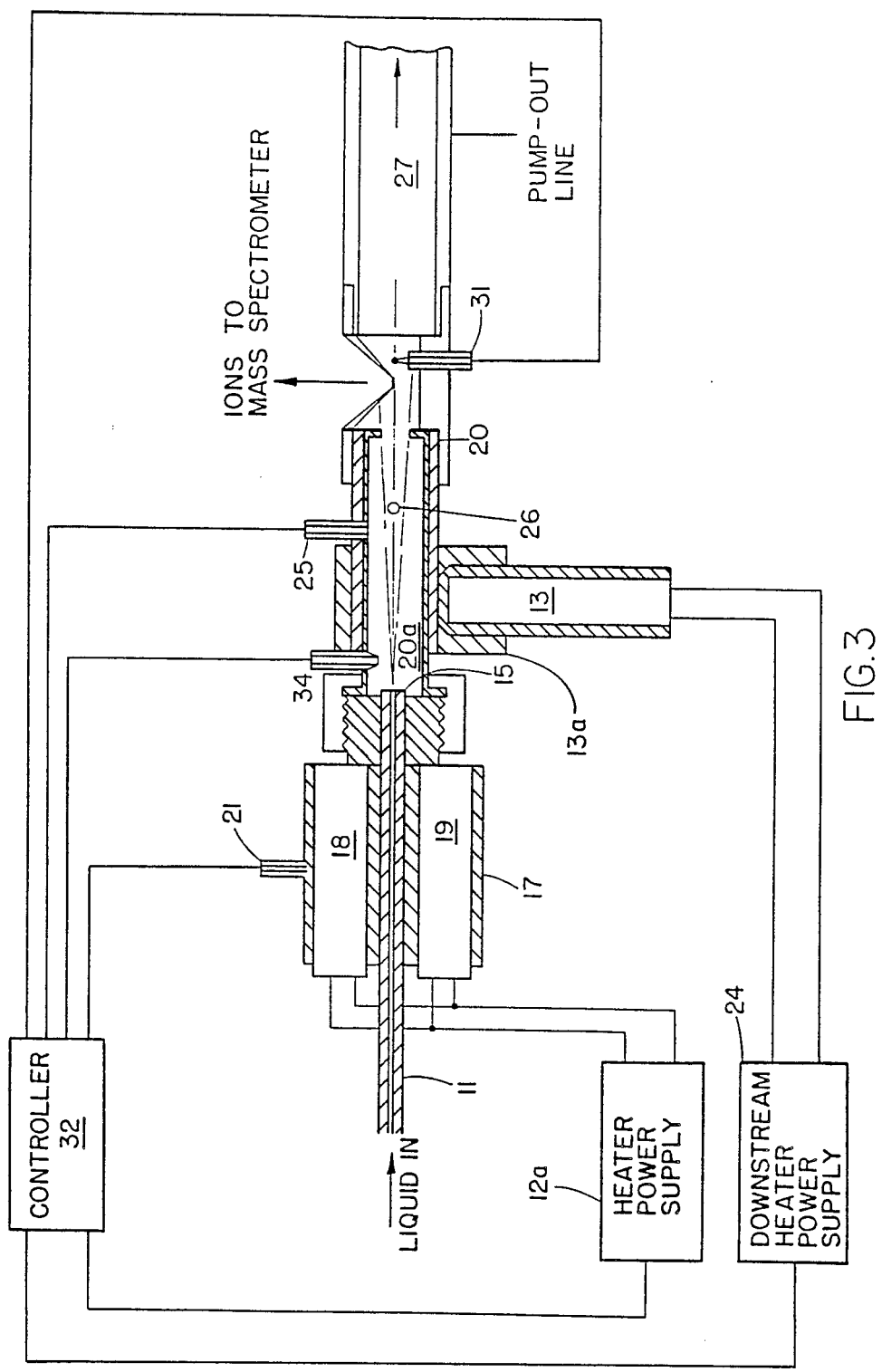
FIG. 3 is a diagrammatic and partially cross-sectioned view of a second alternate embodiment of the present invention.

The operation of the present invention may be summarized with reference to FIGS. 1-3. A capillary tube 11 is provided for partially vaporizing a solution or liquid flowing therethrough. The dimensions of the capillary tube will vary from application to application, but in one embodiment, a capillary tube was formed of a few centimeters of stainless steel tubing having a 0.015 mm ID and a 1.5 mm OD. Heat is supplied to the capillary tube to ensure partial vaporization of the liquid solution to be thermosprayed. While the percentage of solution to be vaporized varies from application to application, the general range of desired vaporization begins at approximately 65% and extends to nearly 100%, but 100% vaporization must not occur at a significant distance (i.e., a few nozzle diameters short of the exit).

Heat for the vaporization is provided in one of three ways:
(a) by direct ohmic heating of the capillary tube,
(b) by conductive heating from a heated block,
(c) a combination of both techniques.

FIG. 1 illustrates a thermospray vaporizer having both heating embodiments. FIG. 2 illustrates an embodiment using only ohmic heating. FIG. 3 illustrates an embodiment using only conductive heating.

As illustrated in FIG. 1, an electric current is provided by power supply 12 by applying a current across a predetermined length of the capillary tube. The output of power supply 12 is applied at the inlet end by contact 16. At the opposite end of the capillary, the circuit is completed by means of contact 14 to the copper block 17. The region of the capillary tube heated lies between contact 16 and block 17. As illustrated in FIG.

1, when current is applied by the heater power supply 12, direct ohmic heating is generated by the capillary 11.

FIG. 1 also discloses a conductive heater 17 having first 18 and second 19 cartridge heaters inserted therein. Block member 17 is preferably a block of high thermal conductivity material such as copper, which is brazed or otherwise intimately secured to capillary tube 11 in a heat conductive manner at the nozzle end 15. A heater power supply 12a supplies the power for the two cartridge heaters 18 and 19 which are operated substantially below their rated power output.

In operation, the device may use either a block heater 17, or the ohmic heating method or a combination of both. The amount of heat necessary to vaporize the liquid solution flowing through capillary tube 11 will vary depending upon the composition of the liquid solution, and variations in flow rate caused by pump irregularities. Block heater 17 is useful in compensating for wide variances in the overall heating load imposed by compositional changes of the liquid solution. The fast response heater provided by capillary 11 and power supply 12 is useful for providing rapid changes in power input to compensate for variations in pump flow rate or unexpected variations in composition.

Inasmuch as the device operates with a predetermined partial vaporization of the liquid solution therein, the device has always heated the liquid to its vaporization temperature, and is functioning within the range of power required to provide the heat of vaporization for the quantity of liquid contained within the capillary 11. As indicated previously, it is desired to operate between 65% up to just less than 100% vaporization. Once 100% vaporization is achieved, the heat of vaporization is no longer available to absorb the heat supplied by the ohmic heater 11, and a high temperature runaway condition will occur. The amount of power supplied by the power supplies 12 and 12a is determined by thermocouples 22 and 34 or 17. It is desired to place thermocouple 22 at a point on capillary 11 before the liquid therein has been vaporized. As will be hereinafter explained, it has been found that the amount of heat necessary to achieve a predetermined degree of vaporization may be determined from the temperature of the liquid at a fixed point before vaporization has begun.

Figure 15:
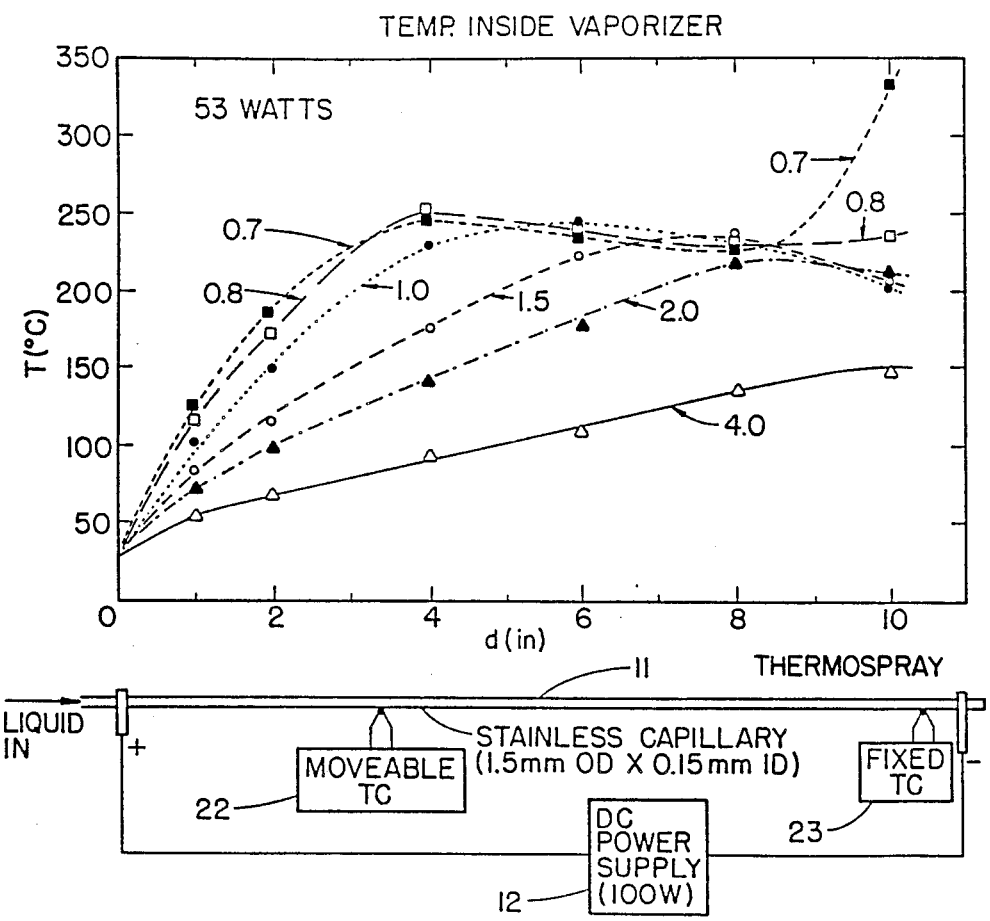
FIG. 15 is a graph and comparative schematic of a thermospray device with a moveable thermocouple. The graph plots the temperature of the capillary as a function of the flow rate and the linear distance traveled by vaporizing liquid in the capillary.

FIG. 15 illustrates the relationship between the flow rate, and the temperature profile along the capillary. A graph has been plotted adjacent to a schematic representation of a thermospray capillary using the ohmic heating method. The temperature along the capillary is plotted for a variety of flow rates beginning at 0.7 ml/min and extending to 4.0 ml/min at a constant power input. The sharp upturn of the 0.7 ml/min curve at 8 inches illustrates thermal runaway that may occur if the sample is completely vaporized before exiting the nozzle.

In practice, a block heater 17 is particularly useful for process flow control or other analytical or detection procedures wherein a known composition is flowing through capillary 11, with little variation in pump flow rate. The thermal time constant of block heater 11 is relatively slow due to the mass of the block and the cartridge heaters themselves. When used as an analytical instrument to vaporize a wide variety of solvents and compounds of interest, the fast response ohmic heater provided by power supply 12 and capillary tube is more desirable, inasmuch as it has a much faster thermal response time then block heater 17.

A controlled expansion chamber 20 receives the thermal spray of vapor and particles from nozzle 15 in the cylindrical space 20. As the particles exit nozzle 15, their internal enthalpy vaporizes some or all of the remaining solvent and some of the molecules of interest into a high speed vapor stream. Cartridge heater 13 supplies additional heat to chamber 20 to prevent recondensation of the solvent around the molecules of interest and to further vaporize any remaining droplets or particles. Cartridge heater 13 receives its power from power supply 24 which is regulated by thermocouple 25 or 31. If desired, the molecules of interest may be ionized by an electron beam or laser passing through chamber 20 as indicated at 26. The vapor jet and molecules of interest are drawn into a pump out line 27 and exhausted The ionized molecules of interest diffuse through the skimmer nozzle 29 and are directed into a quadrupole mass spectrometer generally indicated at 30 by ion lenses 28 Control of the atmosphere in expansion chamber 20 is maintained by means of thermocouple 31 and controller 32 which controls the downstream heater power supply 24. Controller 32 may also receive incoming liquid pressure information from transducer 33 to monitor variations in flow impedance of the capillary 11. This pressure transducer can also provide a measure of fractional vaporization at constant liquid flow rate for a . capillary of known dimensions.

Surprisingly, this system can accommodate vaporizing up to 2 ml/min of liquid directly into the ion source without overloading the pumping systems This corresponds to a gas flow which is about 100 times larger than that used with the mass spectrometer operated in the conventional CI mode. The addition of the mechanical vacuum pump connected directly to the source would only account for about one order of magnitude of increased capacity normally, but locating the pumping line directly opposite the thermospray vaporizer allows the supersonic jet to act as its own ejector pump. Thus the conductance of the pumping aperture is about ten times as high as normal due to the highly directed flow of the jet. It has been found that a 300 1/min mechanical pump is more than adequate to maintain stable performance at flow rates to 2 ml/min. It is essential that the pump be operated with gas ballast to avoid excess accumulation of liquid in the pump oil. Even then, it is important to service the pump frequently (usually daily) to drain out solvent and add pumping fluid.

This problem can be avoided if the pumping line is fitted with a refrigerated trap, for example, cooled by dry ice or liquid nitrogen. Most cf the solvent can then be collected in this trap, thus alleviating these problems with the mechanical pump.

FIG. 2 discloses an alternate embodiment of the invention utilizing only the ohmic heater comprised of heater supply 12 and capillary tube 11. The operation of the heating components of this device correspond in operation to the components previously described with respect to FIG. 1. The control circuit, however, utilizes a comparative amplifier 34 to control the heater power supply 12. In addition, a separate temperature indicator 34 is provided to indicate temperature sensed by the thermocouple on the nozzle end of the capillary. This is used to indicate proper operation of the vaporizer and can be used to trigger an alarm in the event of a thermal runaway. As indicated previously, it has been found that accurate control of the percentage of solvent vaporized may be obtained by placing the control thermocouple 22 on the entrance portion of the capillary where the liquid inside has not yet begun to vaporize.

FIG. 3 discloses an alternate embodiment of the invention using only the block heater which comprises copper block 17 and cartridge heaters 18 and 19. As indicated previously, the copper block 17 is brazed, silver soldered, or otherwise intimately secured to capillary tube 11 in a heat conductive manner. The operation of the heating components of this device correspond in operation with the components previously described with respect to FIG. 1. Controller 32 monitors the temperature at the location of thermocouples 21 and 34 to regulate the heater power supply 12a. In addition, a secondary jet heater and limited expansion volume is defined by chamber 20 which is heated by means of a second block 13a and cartridge heater 13. Controller 32 likewise senses the output of thermocouples 25 and 31 to determine the amount of power supplied by downstream heater power supply 24 to the cartridge heater 13.

Figure 10:
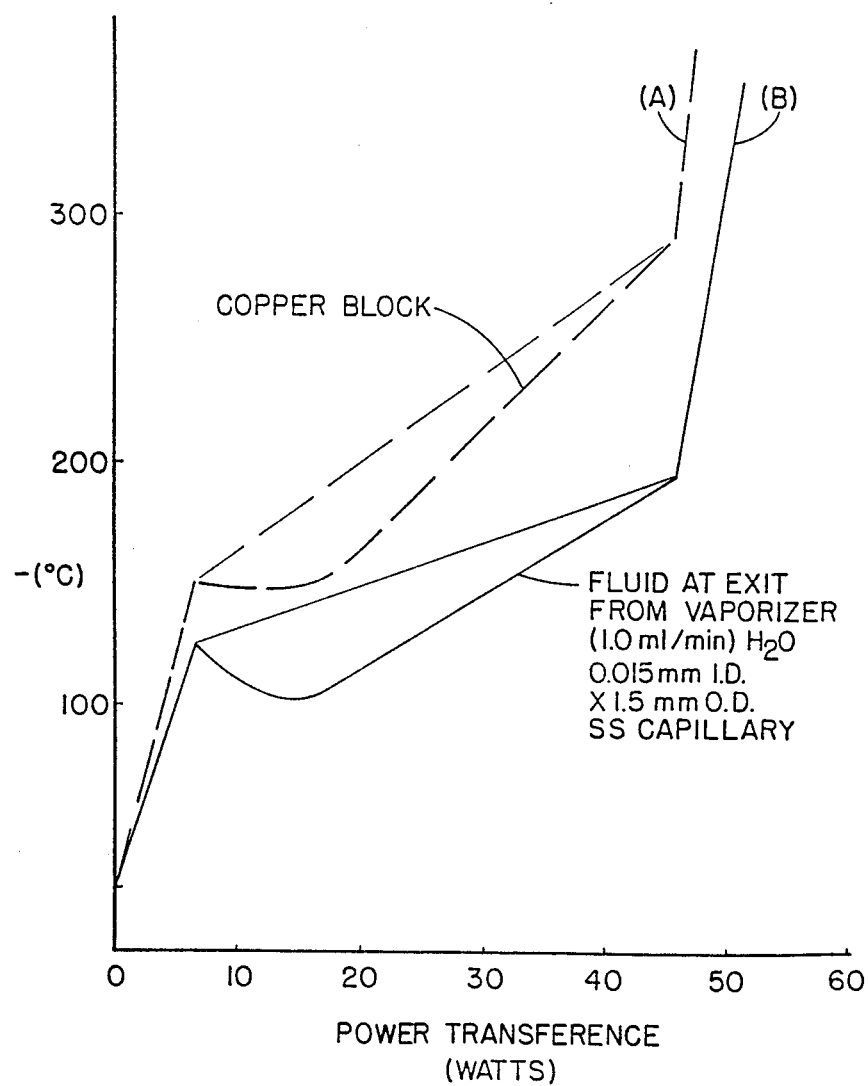
FIG. 10 is a graph illustrating calculated vapor temperatures as a function of power absorbed by the liquid corresponding to a flow rate of 1.0 ml/min through a 0.015 mm ID capillary tube.

An illustration of the amount of power applied, and the effect on the fluid temperature at the exit from the thermospray vaporizer is illustrated in FIG. 10. FIG. 10 is a graph illustrating the calculated vapor temperatures as a function of power absorbed by the liquid corresponding to a flow rate of 1.0 ml/min through a 0.015 mm ID capillary tube. The nominal operating point corresponds to a heater block temperature of about 250° C., and is measured by the thermocouple 21 in FIG. 3. Under these conditions, a supersonic jet is produced with about 75% of the total effluent as vapor at the vaporizer exit. The temperature at the exit is approximately 170° C., and the pressure is about 3 atm. As indicated previously, it is essential for most applications of thermospray that complete vaporization not occur within the vaporizer capillary. This is true both for field assisted vaporization of ions and for transfer of nonvolatile samples to surfaces with efficient solvent removal. Since nonvolatile molecules tend to be concentrated preferentially in the last of the remaining liquid, this prevents thermal degradation of the nonvolatile molecules until their exit from the vaporizer.

As will be discussed hereinafter in more detail, for most applications, it is necessary to supply heat to the vapor jet after it exits the vaporizer into the controlled expansion volume 20 to prevent recondensation and to complete the vaporization. This requires that the jet not be allowed to expand freely into a vacuum, but rather it must be confined so that adiabatic expansion does not proceed indefinitely. Confinement of the jet is necessary for most applications since otherwise the temperature can become extremely low, causing recondensation and other undesirable effects. As indicated previously, heat is added to the confined volume 20 by means of the cartridge heater 13.

As will be hereinafter described in detail, large non-volatile molecules are ejected as intact molecular ions which have been ionized in solution by virtue of the thermospray method. This method appears to be consistent with experimental observations to date, and known physical and chemical processes, which involve the following five steps:

1. Nearly complete vaporization of the liquid at the rate with which it is supplied to the vaporizer produces a super heated mist carried in a supersonic jet of vapor. Nonvolatile molecules are preferentially retained in the droplets of the mist.

2. Droplets of the mist are charged positively or negatively according to the statistical expectations for random sampling of a neutral fluid containing discrete positive and negative charges.

3. Molecular ions clustered with a few solvent molecules evaporate from the superheated droplets assisted by the high local electrical fields generated by the charge on the droplet.

4. Cluster ions rapidly equilibrate with the vapor in the ion source to channels available.

5. Ions diffusing to the sampling apparatus are then transmitted to the mass analyzer or other detecting apparatus.

6. Even if the "soft" ionization created by the thermospray is insufficient to ionize a desired molecule, additional ionization may be provided by an electron beam or laser as indicated at 26.

Theoretical Considerations

Figure 16:
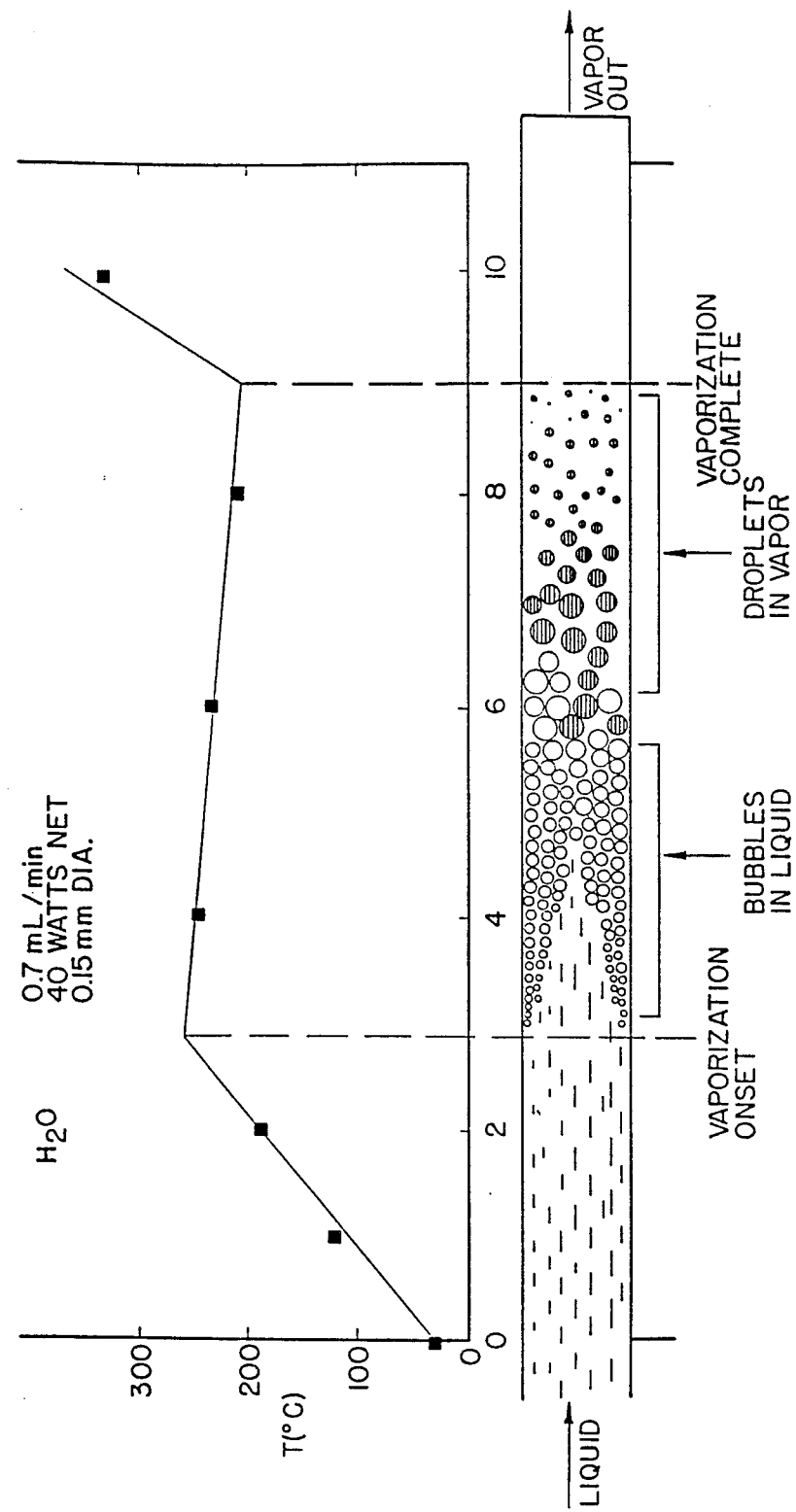
FIG. 16 is a schematic representation of a calculated vaporization at a flow rate of 0.7 mL/min. at 40 watt of input power.

This invention is concerned with the process occurring when a flowing liquid is vaporized as it is forced under pressure through a heated capillary tube. The temperature profiles produced by direct electrical heating of the capillary are illustrated in FIG. 15. In this experiment 53 watts was dissipated in the capillary with water flowing through at rates in the range from 0.7 to 4.0 mL/min as indicated by the parameter in FIG. 15. The experimental result at 0.7 mL/min is compared with a calculated profile in FIG. 16 where the processes occurring in different regions of the heated capillary are represented schematically. At the inlet end the flowing water is heated until vaporization begins. From this point and downstream the temperature remains nearly constant until vaporization is complete since the heat flux is used to provide the latent heat of vaporization. The slight decrease in temperature along the vaporization region results from the fact that the pressure is decreasing toward the exit end. At the point corresponding to complete vaporization the temperature again rises rapidly since only the heat capacity of the vapor is available to absorb the input heat. The power output to the capillary is controlled by feedback so as to maintain the temperature, $T_1$ as indicated by a thermocouple 22 attached to the capillary near the inlet end where no vaporization occurs.

The total power which must be coupled into the flowing liquid to vaporize a fraction, f, of a given mass flow F (g/sec) is $$W = fF\Delta H_v + F(1-f)C_L(T_2 - T_o) \qquad (1)$$

where $\Delta H_v$ is the total specific enthalpy (J/g) to convert liquid at the entrance temperature, $T_o$, to vapor at exit temperature, $T_2$, and $C_L$ is the specific heat capacity of the liquid. The total power coupled into the liquid in the region between the entrance to the vaporization and the location of the thermocouple monitoring $T_1$ is given by $$W_1 = C_L(T_1 - T_o)F \qquad (2)$$

where $T_1$ is the temperature at the control point. If the tube is mounted and insulated so that essentially all of the power dissipated in the tube is coupled into the flowing fluid, then uniform heating of the tube implies that $$W_1/W = L_1/L \qquad (3)$$

where L is the total heated length, and $L_1$ is the length of the heated portion up to the point monitored by $T_1$. Combining equations (1) through (3) and solving for $T_1$ gives $$T_1(0) = T_o + (L_1/L)(T_2 - T_o) \tag{4}$$
$$T_1(f) = T_o + (L_1/L)\{f\Delta H_v/C_L + (1 - f)(T_2 - T_o)\} \quad 0 < f < 1$$
$$T_1(1) = T_o + (L_1/L)\{\Delta H_v/C_L + (C_v/C_L)(T_2 - T_o)\}$$

where $C_v$ is the specific heat of the vapor and the last term in $T_1(1)$ represents the heat input required to heat the dry vapor.

Since the flow rate, F, does not appear explicitly in equation (4), this result implies that the indicated temperature, $T_1$, is linearly related to the fraction vaporized, f. Thus, by controlling the power input so as to maintain $T_1$ constant, the fraction vaporized may be maintained at a constant selected value even though the flow rate may change. Furthermore, this equation predicts how the set point required to maintain a certain fractional vaporization depends on the composition of the fluid. As the fluid composition changes, for example, in gradient elution, the ratio $\Delta H_v/CL$ changes somewhat. If the set point for $T_1$ is changed accordingly, then the fraction vaporized may be maintained constant even though the solution composition may vary from pure water, for example, to pure methanol.

To a good approximation, $T_1$ given by equation (4), is independent of solvent flow rate but is significantly dependent on solvent composition. A hidden dependence on flow results from the fact that $\Delta H_v$ depends on the temperature of the vapor at the exit, $T_v$, which in turn depends on the flow rate.

The rate of vaporization of a liquid at temperature T is given by $$Z = \frac{P_v(T) - P_a}{(2\pi mkT)^{\frac{1}{2}}} \tag{5}$$

where $P_v(T)$ is the equilibrium vapor pressure at temperature T, $P_a$ is the ambient pressure of the vapor, m is the molecular mass, and k is Boltzmann's constant. This expression gives the net flux (no./cm² sec) evaporating. It can be transformed into an effective vaporization velocity by multiplying by the molecular mass and dividing by the density of the liquid to give $$v_v = \frac{(P_v(T) - P_a)}{\rho_L^o} \left(\frac{m}{2\pi kT}\right)^{\frac{1}{2}} \tag{6}$$

If the liquid is completely vaporized, then the vaporization velocity must be at least equal to the liquid flow velocity which is given by $$v_L^o = F/\rho_L^o A \tag{7}$$

where F is the mass flow (g/sec) and A is the cross sectional area of the flow channel in the capillary tube. For complete vaporization, conservation of mass requires that:

$$\rho_L^o v_L^o = \rho_e v_e \tag{8}$$

where $\rho_3$ and $v_e$ are the density and velocity of the vapor at the exit from the capillary, and $\rho_L^o$ and $v_L^o$ are the density and velocity, respectively, of the liquid before it reaches the vaporizer. The maximum velocity with which the vapor can exit the tube is that of the local velocity of sound in the vapor given by $$v_s = (\gamma kT/m)^{\frac{1}{2}} \tag{9}$$

where $\gamma = C_p/C_v$ is the specific heat ratio for the vapor.

Combining equations (8) and (9) and assuming the vapor behaves according to the ideal gas law, we can solve for the pressure of the vapor at the exit from the capillary. The result is given by $$P_e = v_L^o \rho_L^o v_s/\gamma \tag{10}$$

Substituting the exit pressure for $P_a$ in equation (6) and solving for the liquid velocity gives $$v_L = \frac{P_v(T)}{\rho_L^o v_s(T)} \left(\frac{\gamma}{\sqrt{2\pi\gamma} + 1}\right) \tag{11}$$

Figure 4:
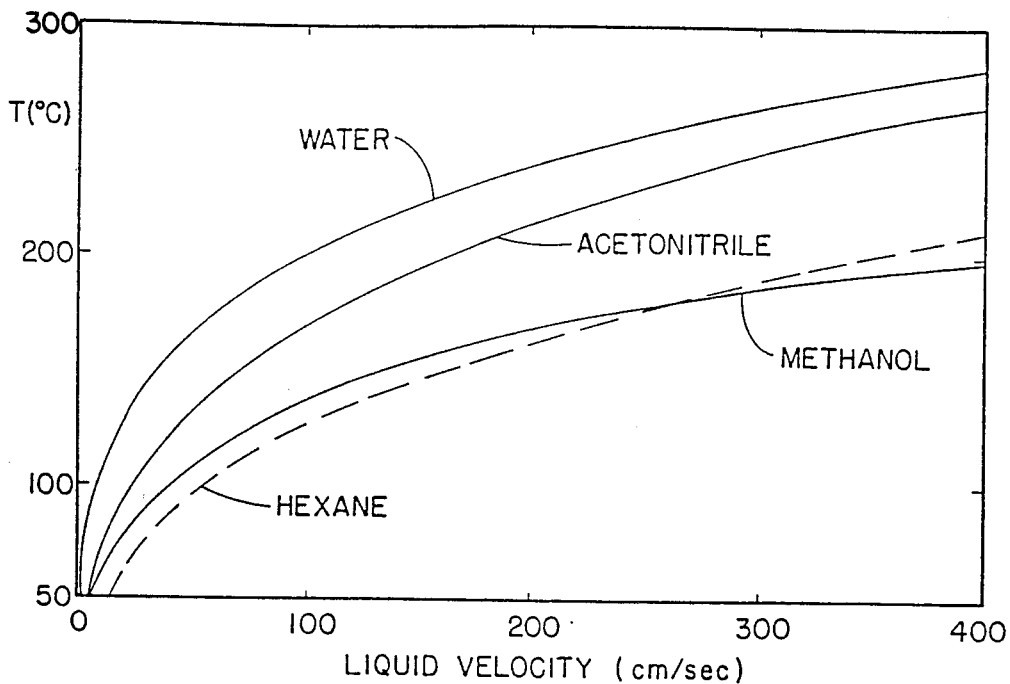
FIG. 4 is a linear plot of minimum vapor temperature for complete vaporization as a function of liquid velocity for several common solvents.

The temperature at which this equation is satisfied corresponds to the minimum temperature of the fluid at which complete vaporization occurs. This equation can be inverted (at least numerically) to give the minimum temperature for complete vaporization as function of liquid flow. Results for several common solvents are summarized in FIG. 4. If the heat supplied to the liquid is more than required to reach this temperature (for a given flow rate) vaporization will occur prematurely and superheated, dry vapor will emerge from the capillary. If the heat supplied is slightly less that the critical value, then a portion of the liquid is not vaporized and will emerge along with the vapor jet as small entrained droplets. For most applications for thermospray it appears that the best operating point corresponds to a fluid temperature at which partial but nearly complete vaporization occurs. In this range the residual droplets tend to be relatively small and are accelerated to high velocities by the expanding vapor. Since the vapor pressure is a very steep function of the temperature, it is essential to have very precise control of the temperature if a stable fraction vaporized is to be maintained at nearly complete vaporization.

Figure 17:
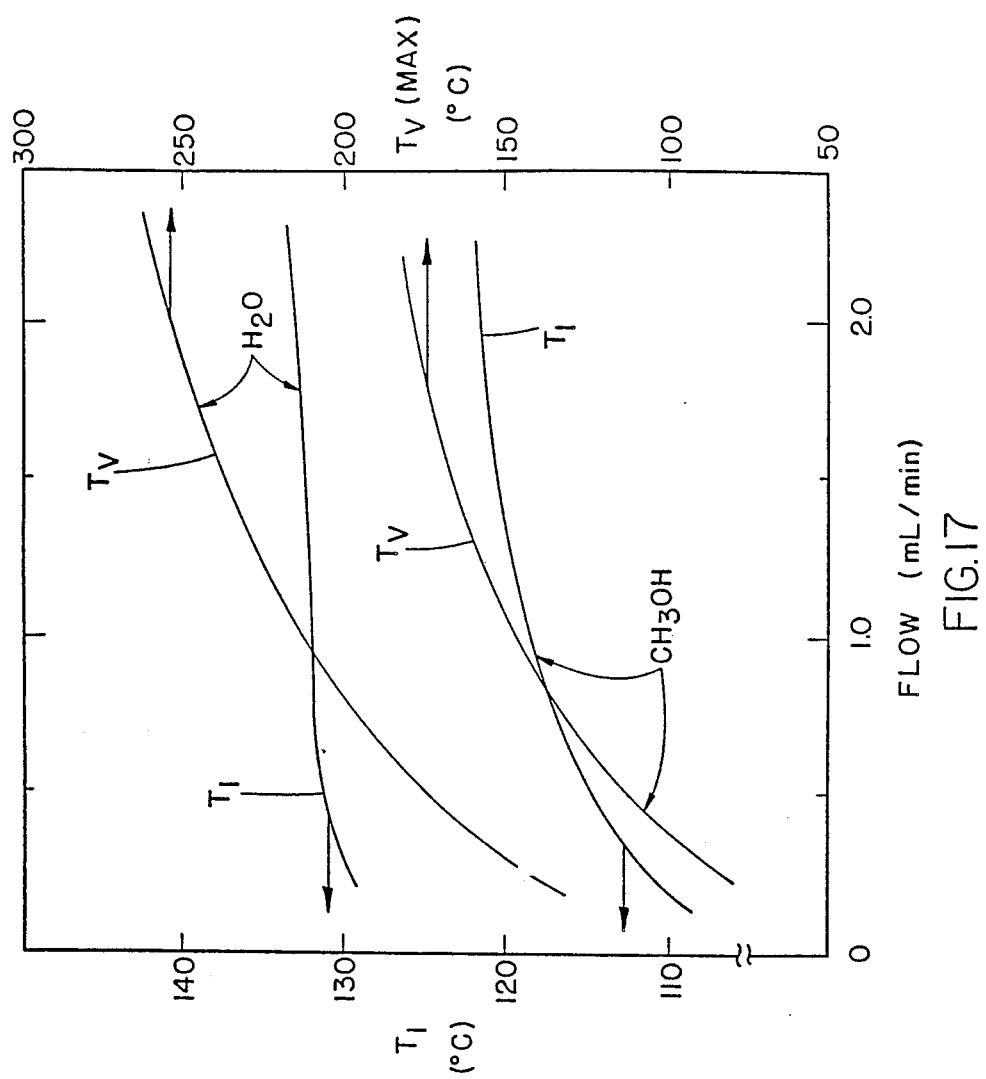
FIG. 17 is a graph of control point temperature, $T_1$, and vapor exit temperature corresponding to complete vaporization at the exit.

Thus we can calculate for a given ratio $L_1/L$ the temperature, $T_1$, which corresponds to a certain fractional vaporization of any fluid at any flow rate. Results for water and methanol flowing through a 0.15 mm diameter capillary with $L/L_1 = 6$ given in FIG. 17. As can be seen from the figure, the dependence on flow rate is rather small, being on the order of 1° C. for 1 mL/min change in flow rate of water, but the dependence on composition is fairly substantial, corresponding to about 15–20° C. difference between water and methanol at the same flow. For many purposes the flow rate dependence may be unimportant; however, if 99% or more vaporization is required in a given application, then the set point must be adjusted whenever large changes in flow rate are made. It is clear, however that this method of control provides a basis for correcting for the small flow fluctuations introduced by typical LC pumps provided the overall response of the control system and vaporizer is sufficiently fast.

Figure 9:
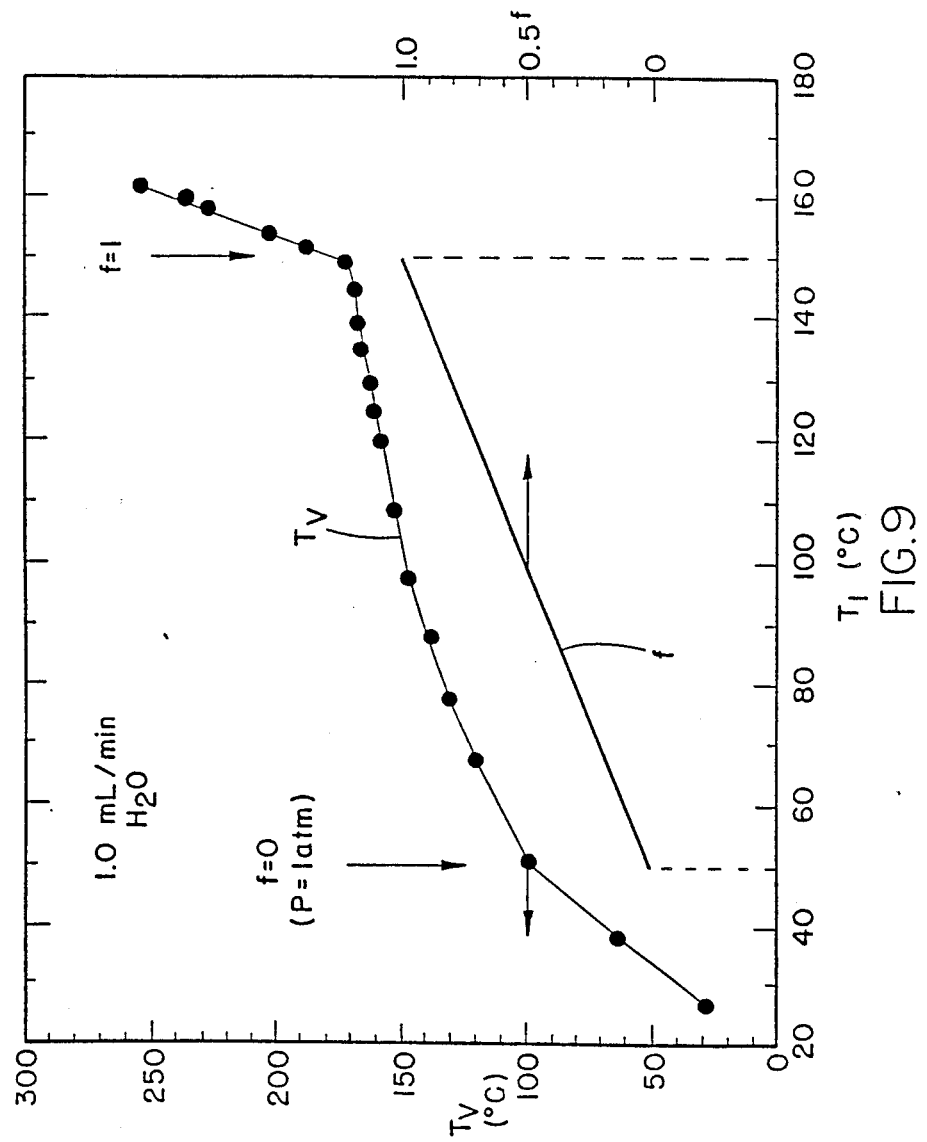
FIG. 9 is a graph illustrating the variations in the vaporizer exit temperature resulting from various control point temperature $T_1$, at a flow rate of 1.0 mL/m.

Samples of results on the variation of vaporizer exit temperature with control point temperature, $T_1$, are shown in FIG. 9 for water at 1 mL/min being vaporized at atmospheric pressure. These results were obtained using a capillary which according to the manufacturer's specifications was between 0.10 and 0.15 mm ID. The sharp upward break in exit temperature at $T_1=150°$ C. corresponds to complete vaporization (f=1) at the exit. The downward break at $T_1=50°$ C. indicates the onset of vaporization (f=0). With this particular probe, the fraction vaporized is given by $f=T_1-50$, for $50 \leq T_1 \leq 150°$ C. After correction for convective losses, these results are generally in good agreement with theoretical expectations, except that the exit temperature (170° C.) at which f=1 corresponds to a liquid velocity of only about 50 cm/sec. This is about one half the velocity expected for 1 mL/min flowing through a 0.15 mm ID capillary. Subsequent measurements of the capillary showed that the ID was, in fact, 0.2 mm as indicated by the above results. Performance obtained with the oversized capillary is generally inferior to that obtained with diameter of ca. 0.1 to 0.15 mm, presumably because the maximum exit temperature is too low for efficient vaporization of less volatile solutes.

Figure 18:
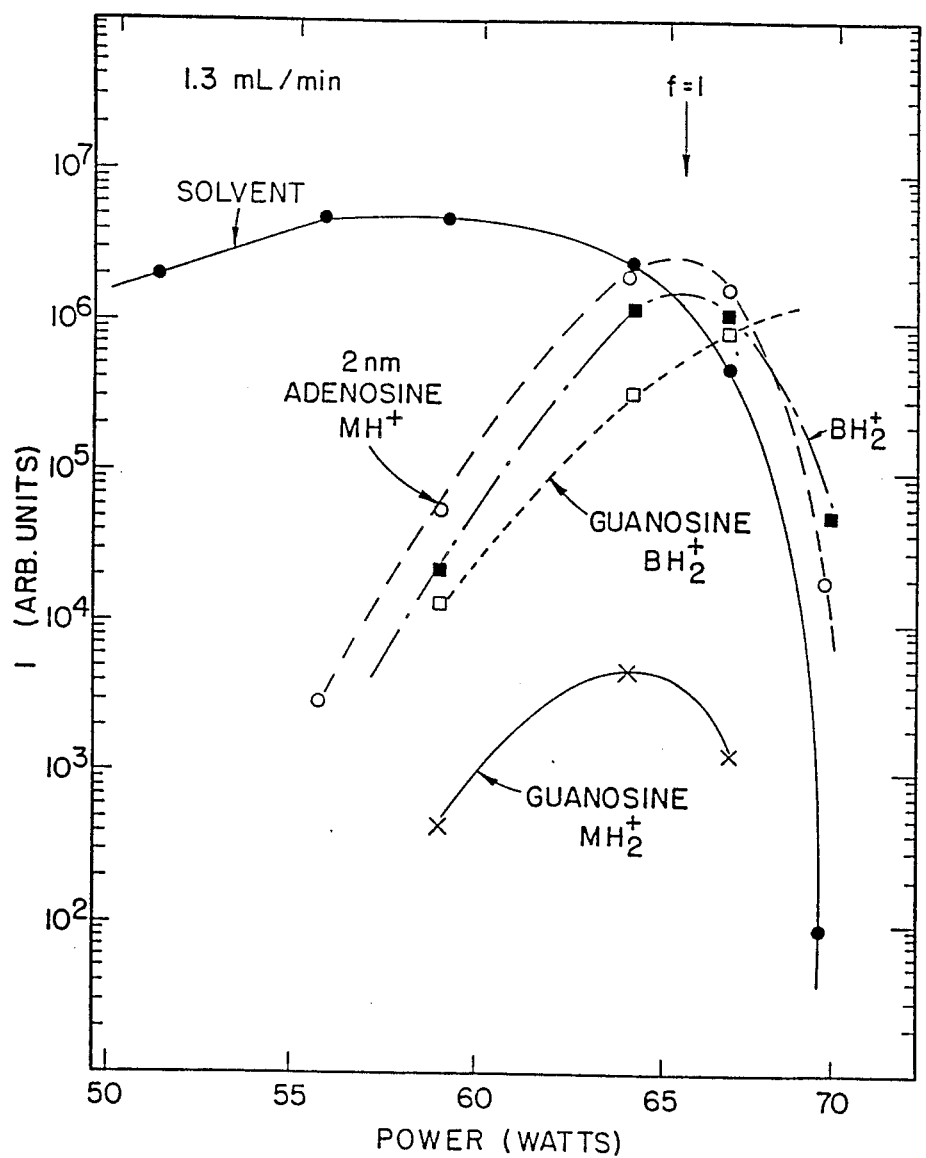
FIG. 18 is a graph of Ion intensities as functions of power applied to the vaporizer with no downstream heating of the jet.
Figure 19:
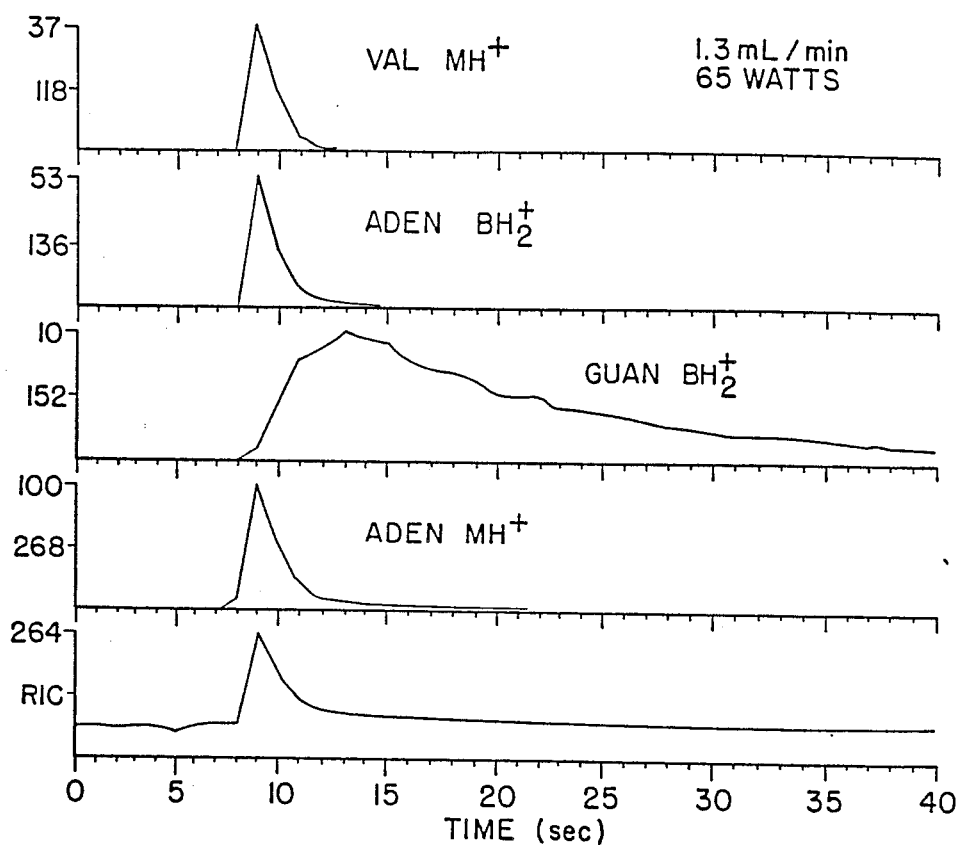
FIG. 19 is a series of mass chromatograms for injections of test solution at vaporization power of 65 watts under the conditions illustrated in FIG. 18.

The importance of vaporizer geometry and exit temperatures for efficient vaporization and ionization of nonvolatile molecules is illustrated by the results shown in FIG. 18. In this experiment the vaporizer was placed within 0.5 cm of the aperture for sampling ions into the mass analyzer and the ion source heater was turned off. In this mode of operation almost all of the vaporization and ionization occurs in the vicinity of the vaporizer tip. These results were obtained with 0.1 M aqueous ammonium acetate flowing at 1.3 mL/min. A test solution containing $10^{-4}$ M concentrations of valine, arginine, adenosine, and guanosine was prepared using the 0.1 M buffer, and 20 ul aliquots were injected as the power input to the thermospray vaporizer was varied. The results of FIG. 18 cover the range from 80 to 100% vaporization of the solvent. The response for both the $MH^+$ ion and the $BH_2^+$ fragment of adenosine maximize near f=1, while the response for $NH_4^+$ and its clusters with the solvent shows a broad peak at lower input power. The protonated molecular ion for valine (not shown) gives a response similar to that for adenosine. A very weak signal corresponding to protonated guanosine is observed; this intensity is about 3 orders of magnitude less than that for adenosine. The $BH_2^+$ fragment of guanosine is more intense, and continues to rise beyond f=1. It appears that this fragment may be produced from guanosine which has deposited on the inner surface of the capillary and pyrolyzed. This conclusion is supported by observation of the time profiles of the various ions following the injections at f=1 and above. As shown in FIG. 19, the mass chromatograms for valine and adenosine show the expected narrow peaks, while the guanosine fragment intensity persists for at least a full minute after injection. Under these conditions the $MH^+$ ion for arginine was not detected, indicating that its response was less than $10^{-4}$ that for adenosine.

Figure 20:
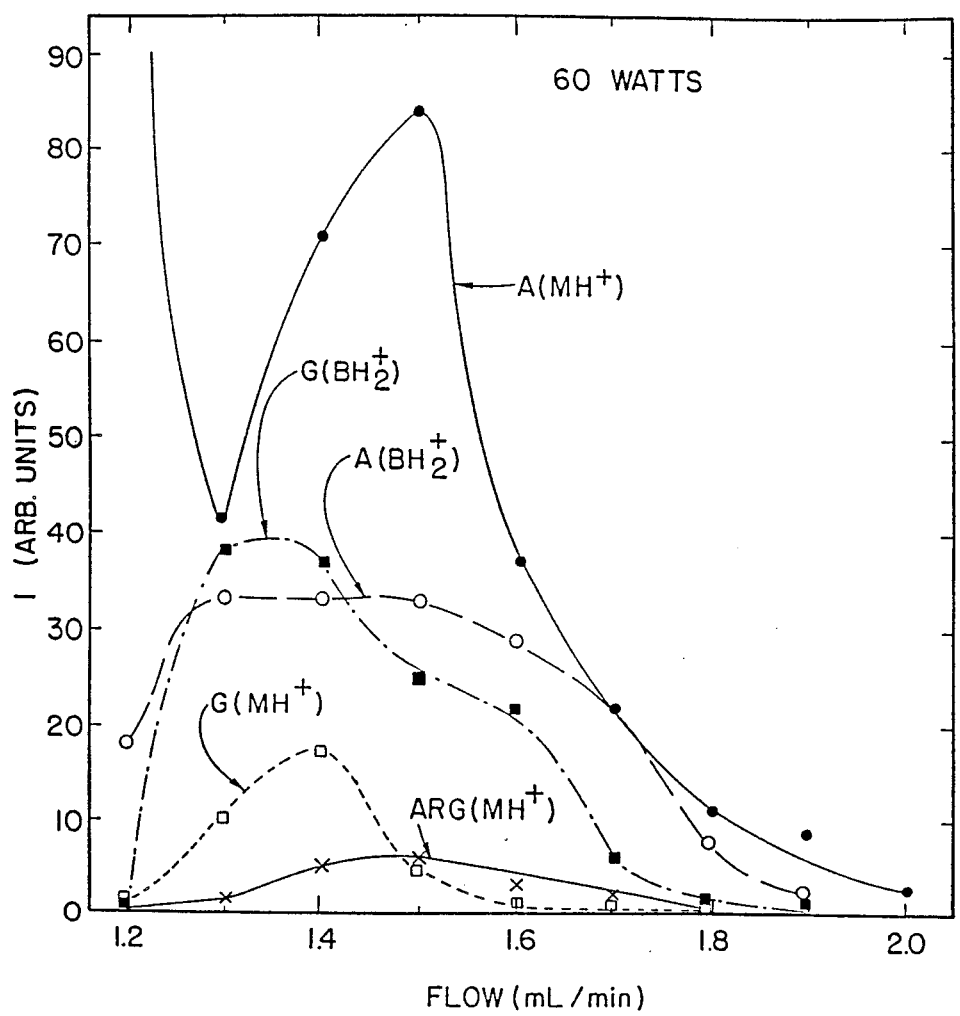
FIG. 20 is a graph of ion intensities vs. flow at constant vaporizer power with downstream heating of the jet to 250° C.
Figure 21:
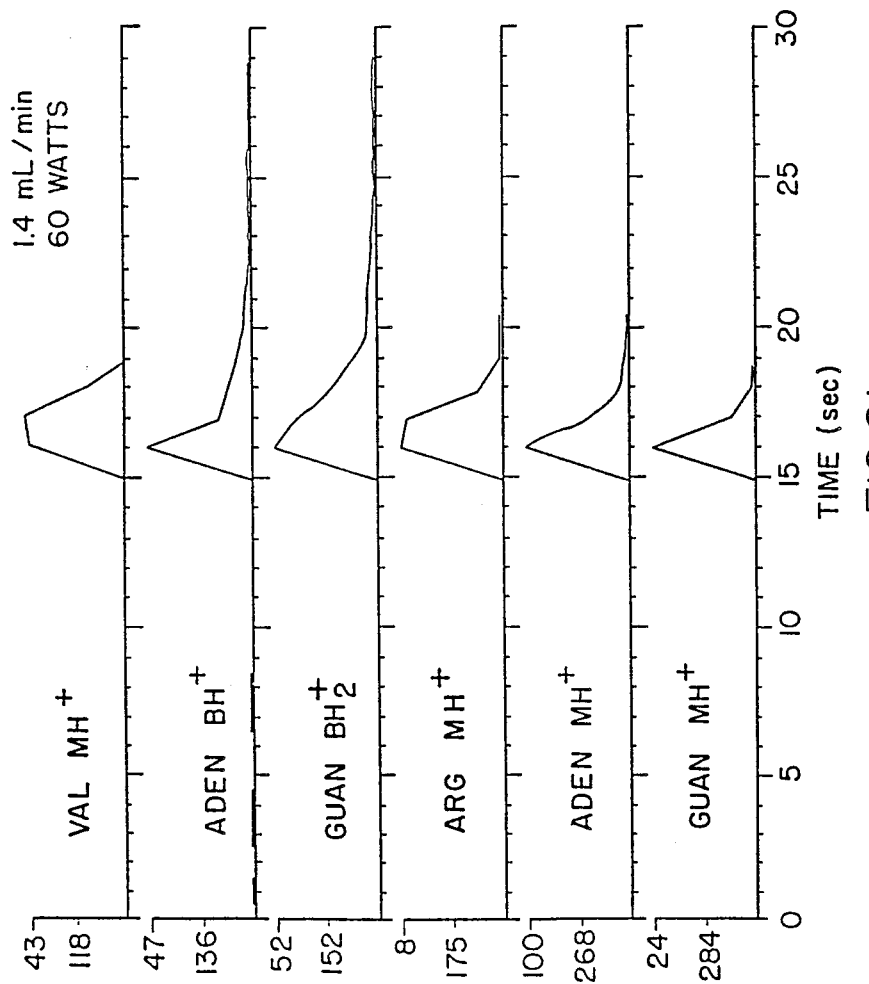
FIG. 21 is a series of mass chromatograms for major ions observed at 1.4 mL/min under the conditions illustrated in FIG. 20.

By increasing the distance between the vaporizer and the ion sampling aperture and strongly heating the ion source, vaporization of the droplets in the thermosrpay jet can be made to occur downstream from the vaporizer. An example of results obtained with this more usual mode of operation is shown in FIG. 20. In this experiment the power into the vaporizer was maintained constant at about the level required to completely vaporize 1.2 mL/min and the vaporizer tip was located about 4 cm from the ion exit aperture. The power input to the source heater was controlled so as to maintain the temperature of the vapor stream at 250° C. as monitored by a thermocouple located near the center of the flowing stream and at a point about 3 mm downstream from the ion exit aperture. In this case the fraction vaporized at the vaporizer exit varies from about 1 at 1.2 mL/min down to about 0.6 at 2 mL/min. Adenosine and valine both maximize near f=1, but show a second maximum in the vicinity of 1.4 to 1.5 mL/min, which corresponds to 80-85% vaporization. Arginine and guanosine $MH^+$ intensities also maximize in this region as do the fragment ion intensities. In this operating mode, maximum response for arginine and guanosine are about 10 and 25%, respectively, of that for adenosine. Mass chromatograms for the major ions obtained at 1.4 mL/min are shown in FIG. 21. A very small amount of tailing is observable on the $BH_2^+$ fragments of both adenosine and guanosine, indicating that some pyrolysis may be occurring, but this effect is very small compared to that shown in FIG. 19 for guanosine.

Figure 22:
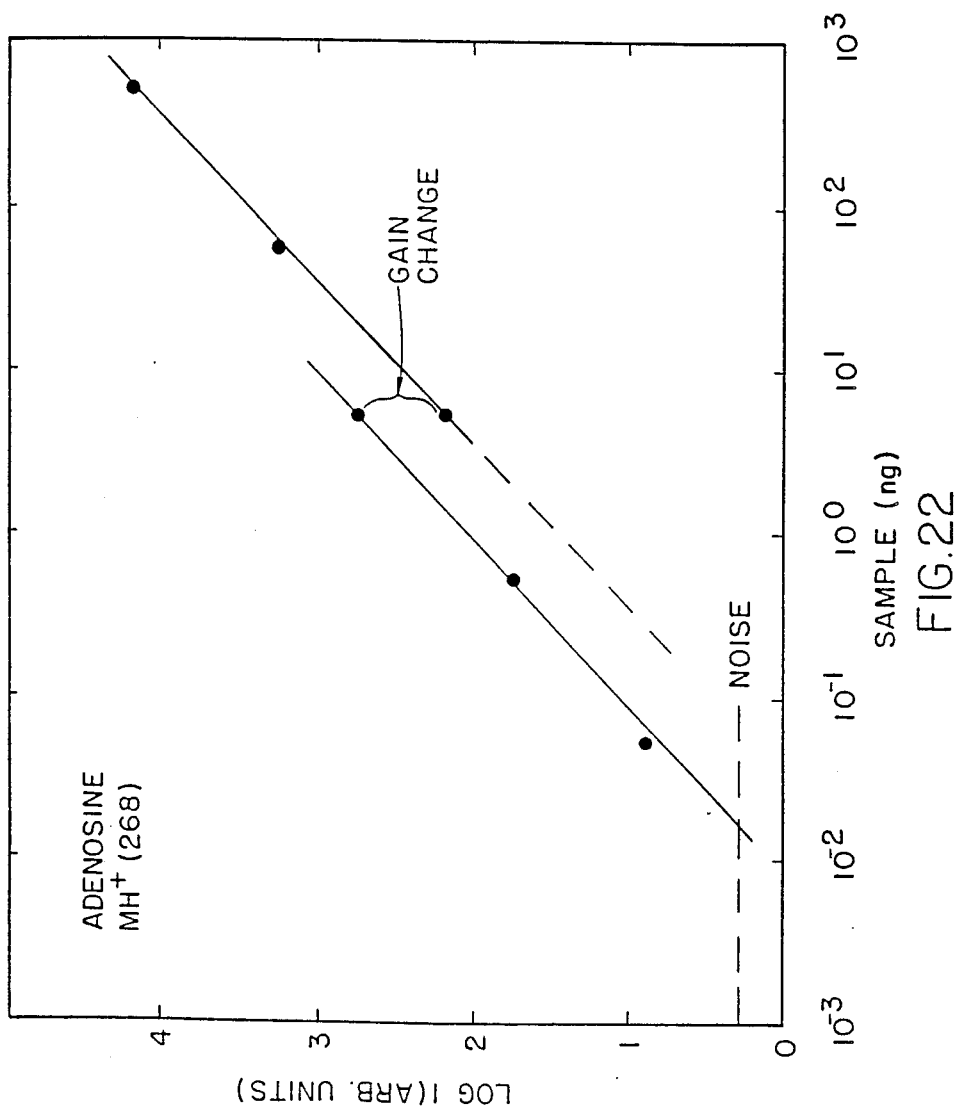
FIG. 22 is a graph of response vs. sample injected for adenosine at optimum sensitivity for the conditions illustrated in FIG. 18.

The best choice of operating conditions depends to some extent on the properties of the samples and the information desired. For modestly volatile compounds, e.g., adenosine and valine, it is possible to accomplish essentially complete vaporization within or just outside the tip of the thermospray vaporizer and obtain quite high sensitivities As an example, measured responses to a series of injections of adenosine standards under conditions of nearly complete vaporization are illustrated in FIG. 22. In this example the detection limit (S/N=2) is about 20 pg and the linear dynamic range is at least $10^5$. On the other hand, this operating condition is not useful with this particular vaporizer for less volatile samples such as guanosine, arginine, and others.

By operating at lower fractions vaporized within the thermospray and applying copious downstream heat, a more nearly uniform sensitivity is usually obtained. As indicated in FIG. 20, some sacrifice in sensitivity for the more volatile compounds may result, but the sensitivity for less volatile components may be significantly improved.

The importance of having the droplets exit with high velocity can be seen by considering the effects of the rapid adiabatic expansion that occurs after the vapor and its entrained droplets exit from the vaporizer. For a free jet exit, the Mach number downstream according to the work of Ashkenas and Sherman is given by:

$$M = A \left( \frac{x - x_o}{d} \right)^{\gamma - 1} - \frac{1}{2A} \left( \frac{\gamma + 1}{\gamma - 1} \right) \left( \frac{d}{x - x_o} \right)^{\gamma - 1} \quad (12)$$

where A=3.82, $X_o$32 0.6 d, and d is the nozzle diameter and = is distance from the nozzle in units of nozzle diameters. The Mach number is defined as the ratio of the axial velocity $u_g$ to the local speed of sound given by equation (9). For an adiabatic expansion we have:

$$C_p T_o = (\tfrac{1}{2}) m \, u_g^2 + C_p T \quad (13)$$

which can be inverted to give the temperature downstream as:

$$T = T_o \left(1 + \frac{(\gamma - 1)}{2\gamma} M^2\right)^{-1} \quad (14)$$

and $$P = P_o^{\gamma/\gamma - 1} \quad (15)$$

where $T_o$ and $P_o$ are the temperature and pressure, respectively, of the vapor at the exit. The adiabatic expansion continues until the pressure in the jet is comparable to the pressure of the background gas.

This is the location of the Mach disc relative to the nozzle. Beyond this point heat transfer between the jet and the background gas becomes important and the jet undergoes a normal shock with the velocities rapidly relaxed back to the local thermal velocity. Between the nozzle and the Mach disc, the supersonic vapor stream controls the environment, and any evaporation of the remaining solvent. Downstream of the Mach disc, the surrounding atmosphere may be controlled.

During the free jet expansion the entrained liquid droplets become highly superheated (relative to the surrounding vapor) and undergo adiabatic vaporization in which the heat of vaporization for the droplet is supplied by its internal enthalpy The rate of vaporization of a spherical droplet is given by:

$$dr/dt = v_v(T) \quad (16)$$

where the vaporization velocity $v_v(T)$ is given by equation (2). Since the process is adiabatic the result is:

$$dH = (-\Delta H_v\rho)dV + C_L\rho V dT = 0 \quad (17)$$

Combining these two equations (16) and (17) gives:

$$dT = \frac{\Delta H_v}{C_L} \frac{dr}{r} \quad (18)$$

which can be integrated to give:

$$T_o - T = (\Delta H_v/C_L)ln(r_o/r) \quad (19)$$

If the droplet moves with the velocity $v_p$ then the foregoing equations (13) and (15) can be combined and integrated to give an explicit expression relating to the distance X that the particle travels and its temperature. This expression is given by:

$$X = \frac{v_p\, r_o C_L}{\Delta H_v} \int_{T_o}^{T} \frac{e^{-(\frac{C_L}{\Delta H_v}(T_o - T))}}{v_v(T)}\, dT \quad (16)$$

where the variation in the particle velocity with distance has been neglected.

Rapid vaporization of the superheated droplets exiting the vaporizer capillary causes the temperature of the droplets to initially fall more rapidly than the temperature of the vapor in the supersonic jet. Within a short distance downstream (about one nozzle diameter or less) conditions are such that recondensation on the droplets may occur. Fast particles cross through this region sufficiently quickly that very little growth occurs, and throughout the remainder of the free jet expansion the temperature of these particles is above that of the vapor, and the vapor pressure of the particles is above the pressure of the vapor in the surrounding jet. Thus, the fast particles will continue to vaporize throughout the free jet expansion, although slowly because the temperature has been reduced by adiabatic vaporization. Slow particles, on the other hand, will tend to approach equilibrium with the vapor in the jet. In this case, after the initial vaporization, the temperature of the slow particles will follow closely that of the vapor. Particle and vapor temperatures as a function of distance from the nozzle are sketched in FIG. 8. FIG. 8 plots absolute temperature as a function of distance downstream from the vaporizer for vapor and for fast and slow particles or droplets. If the environment surrounding the free jet is heated, then downstream of the Mach disk heat transfer from the surrounding medium becomes effective and the temperatures of the vapor and particles rises. In this region the particle temperature will lag behind the vapor temperature, with the lag being largest for the slower and larger particles.

A particle exiting the nozzle with sonic velocity will be rapidly accelerated to supersonic velocity and otherwise will react only weakly with the vapor. The diameter of these particles will decrease monotonically with distance. High velocity (but subsonic) particles will initially vaporize in a shorter distance, but then may grow slightly as they pass through the supersaturated region. Slow particles will grow throughout the free jet expansion and will enter the heated region downstream of the Mach disk, much larger and much colder than the smaller droplets. The average droplet diameter is closely correlated with the fraction of the liquid vaporized within the thermospray vaporizer. As the fraction vaporized approaches unity the droplet diameter becomes small and the velocity high.

Design and Control of the Thermospray Vaporizer

From the foregoing theoretical considerations the thermospray vaporizer may be designed for any application. The important design parameters for the vaporizer are the following:

(1) The inside diameter of the vaporizer capillary.
(2) The length of the heated zone.
(3) The maximum permissible temperature at the inner surface of the capillary.
(4) The thermal time constant of the heater or heaters.

In the foregoing theoretical discussion, it was assumed that the liquid channel is of uniform cross section. While it significantly complicates the analysis and makes construction somewhat more difficult, it may be advantageous in some cases to have the cross section smaller near the exit. This would allow higher temperatures and velocities at the exit while allowing lower liquid velocities in the region where the major part of the heat transfer is occurring.

In choosing the optimum values for the above parameters, the following information about the operating conditions is needed:

(1) The solvent flow rate and composition.
(2) The degree of vaporization required.
(3) The maximum permissible temperature of the fluid in the vaporizer.
(4) The magnitude and time constants of uncontrolled variations in flow rate or solvent composition.

The other important considerations in designing a thermospray system are the methods used for determining the state of the fluid exiting the vaporizer and the way in which this information is used to control the power input to the vaporizer to achieve the desired operating condition.

Design of Thermospray Vaporizer

The range of operating temperatures which are used depends to a great extent on the application and the kinds of samples to be analyzed. For example, it has been found for direct LC-MS on nonvolatile compounds, separated by reversed phase HPLC using water-methanol or water-acetonitrile, that vapor temperatures in the range from ca. 150 to 250° C. give good results in most cases. These conditions are compatible with a 0.15 mm capillary and flow rates in the range from 0.5 to 2 ml/min, corresponding to liquid velocities in the range of ca. 50 to 200 cm/sec. At these velocities, a heater length on the order of 3 cm is adequate to provide, sufficient heat transfer without exceeding the limitations on surface temperature.

To adapt this technique to microbore liquid chromatography, where the flow rates may be an order of magnitude or more lower, and to maintain comparable operating conditions, the area of the capillary channel must be reduced as the flow rate is reduced in order to maintain a similar range of liquid velocities and corresponding exit temperatures. In the case of relatively volatile or thermally labile samples, it may be desirable to limit the maximum permissible temperature in the vaporizer. This implies that the liquid flow velocity must be limited, and a given solvent flow rate and composition may dictate an increase in the diameter of the capillary channel.

The ability of the control system to correct for variations in liquid flow or solvent composition depends mainly on the time constant of the temperature sensor and of the vaporizer heater. These time constants are determined by the heat capacities and the rates of energy input and dissipation. To allow correction for rapid changes, for example due to pump imperfections, it is important to keep the masses of the heaters and sensors rather small.

From theoretical consideration of the desired characteristics of the thermospray vaporizer, the embodiment illustrated in FIG. 2 using only direct Joule heating of the capillary tube may be superior for some applications. This approach allows the thermal mass of the heater to be small compared to that of the flowing liquid, and allows the use of a very short time constant. This approach also requires a power supply with fast response since otherwise a momentary flow stoppage can lead to drastic overheating. One of the practical disadvantages of this approach is that it requires rather high electrical currents and is most conveniently done using a relatively long heated length of capillary. We have found a stainless steel capillary of 0.015 mm I.D. × 0.15 mm O.D. × 30 cm long to be a convenient choice. Capallaries of smaller dimensions have also been used successfully but these are more difficult to fabricate into practical vaporizers.

The rather long heated length normally used in the directly heated capillary vaporizers may cause some loss in efficiency for direct thermospray vaporization of ions from solution since a significant number of ions may be produced inside the capillary and lost due to either gas phase or wall recombination. Another problem with these vaporizers is that it is difficult to make the required electrical connection at the nozzle end without leaving a small portion which is not sufficiently heated. This allows the temperature of the vapor to drop before exiting the nozzle and may also cause some loss in efficiency.

One approach to combing the best features of both vaporizers is shown in the embodiment shown in FIG. 1. In this case the heater power is split between the two vaporizers with typically ⅓ to ⅔ being supplied by the ohmic capillary heater and the remained by the block heater. The capillary heater is usually considerably longer (ca. 30 cm) than the block heater (ca. 3 cm). This combination allows the fast response of the capillary heater to be employed to correct for flow variations while the block heater assures that the vaporizer temperature is properly controlled at the exit nozzle and that the final portion of the vaporization within the capillary occurs.near the nozzle.

The performance of all of these vaporizer configurations depends strongly on the control system used and the location of the sensors used for determining the state of the fluid exiting the vaporizer. One of the most effective approaches is the use of a temperature sensor attached to the capillary vaporizer in the region within which vaporization has not yet begun. This sensor is useful with both the directly heated capillary and with the combination described above. If the vaporizer heater power supply is controlled by feedback from this sensor so as to maintain this temperature constant, then very stable operation is obtained even though much larger flow variations may occur.

A temperature sensor located in the vapor jet downstream of the mach disk may be used in a similar manner to control any of these vaporizers While this approach is somewhat more generally applicable, it is somewhat affected by other parameters such as the heat supplied to the ion source block; thus it is not as directly related to fractional vaporization and is neither as reliable nor as stable as the former.

Another way of monitoring the performance of the vaporizer is the measure the pressure in the liquid upstream of the vaporizer as indicated at 33 in FIG. 1. This pressure corresponds to the pressure drop due to flow of liquid through the tube plus the pressure produced by the vaporization. Variations of pressure with temperature are dominated by the second contribution; and for a given liquid composition and flow velocity it is uniquely related to fraction vaporized. One of the potential problems with this approach is that the relationship between pressure and temperature may change, for example, due to fluctuation in the LC pump or from partial occlusion of the liquid channel. If such an occlusion occurs upstream, the pressure would increase due to a change in liquid flow impedance even though the vaporization conditions had not changed, and the pressure indication would not provide the correct input for control of the vaporizer. On the other hand, if partial occlusion occurs at or near the exit of the vaporizer, both the exit temperature and the pressure will rise together at constant power input (and constant fraction vaporized). If the power is adjusted to keep either the exit temperature or upstream pressure constant, the fraction vaporized will decline as the vapor velocity increases due to an occlusion at or near the tip. At a constant flow rate and solvent composition, this condition can be detected by monitoring the power input to the heater.

The exit temperature, the upstream pressure, and power input are related to the liquid flow velocity and fractional vaporization as discussed above. The liquid flow rate and solvent composition are nominally controlled by the liquid pumping system. If the liquid flow rate and composition, power input, liquid pressure, and exit temperature are all monitored, then the fractional vaporization is uniquely determined independent of any uncontrolled changes in effective vaporizer diameter which might occur as a result of partial occlusion. Since modern liquid chromatographic pumps are often operated under control of a microprocessor, it appears feasible to select the desired solvent flow rate, composition and fractional vaporization, and to program the microprocessor to automatically adjust conditions so that the fraction vaporization is maintained constant both with changes in solvent composition and flow rate and with uncontrolled changes in vaporizer characteristics which might be introduced by pump variations or partial occlusion of the flow channel. In the event that such occlusions causes the exit temperature or liquid pressure to exceed preset limits, an alarm showing incipient failure could be triggered.

Applications

The extent of vaporization which is desirable depends to some extent on the particular application, but it appears that most applications which we have considered so far involve operation at substantial vaporization where both the particle velocities and the temperatures of the droplets and vapor are highest. As the jet undergoes an adiabatic expansion, the temperatures of both the vapor and the droplets decrease rapidly leading eventually to complete quenching of further vaporization. For most applications it appears desirable to limit the duration of the adiabatic expansion so that the temperature in the jet does not get too low. In many cases additional heat is added downstream of the Mach disk to effect further vaporization. Individual cases are discussed below.

1. Direct Production of Ions in On-Line LC-MS

If the droplets or particles produced in the thermospray vaporizer are charged sufficiently, then ions as well as neutrals may be vaporized. If the solution being vaporized contains ions in solution, then the droplets are charged by the symmetric charging mechanism. Other charging mechanisms may also be involved, and other methods of adding charge (e.g. electrical discharge) may also be employed. While a completely satisfactory theory of field-assisted vaporization of ions from liquid surfaces is not yet available, it appears that surface field strengths on the order of $10^8$ V/m are required for evaporation rates for ions to be comparable to those for neutrals It appears that some of the droplets produced when thermospraying aqueous electrolytic solutions (e.g. 0.1 M ammonium acetate) may initially be small enough and highly enough charged to emit ions as they exit the vaporizer nozzle. However, due to the rapid cooling that results from evaporation of the droplets during the adiabatic expansion, this ion emission will not persist unless some additional heat is added downstream to assist in further vaporization of both ions and neutrals.

The efficiency of thermospray ionization is very sensitive to vaporizer conditions. Total ion currents obtained from thermospray ionization of 0.1 M aqueous ammonium acetate measured as a function of vaporizer temperature and flow rate are summarized in FIG. 5. These results were obtained by operating the quadrupole with only RF excitation so as to transmit all of the ions and by collecting the ions on a Faraday cup at the quad exit. No external source of ionization was used for these experiments and no electrical fields were employed inside the ion source. These results were obtained for positive ions, but approximately equal intensities of negative ions are also produced and their behavior with temperature and flow rate is similar.

Figure 5:
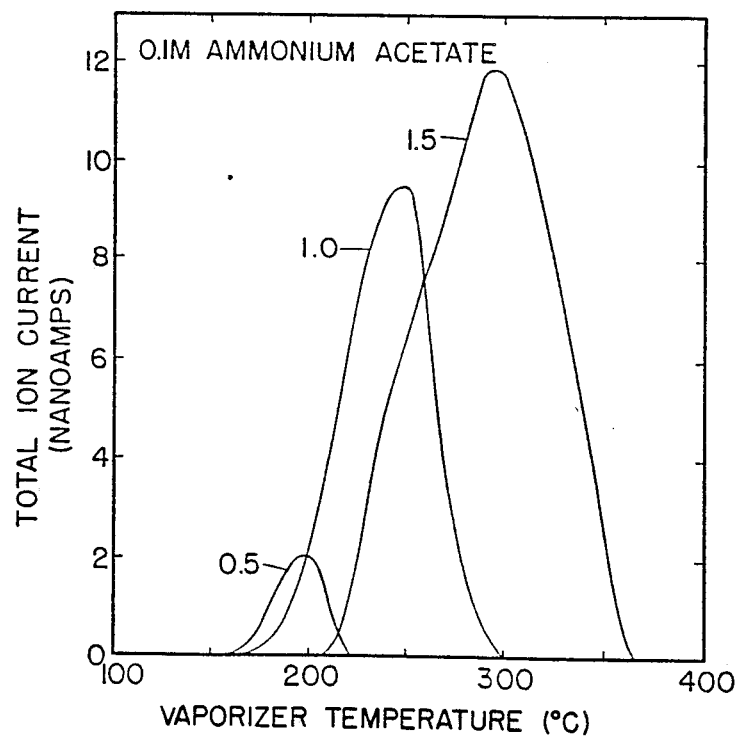
FIG. 5 is a graph illustrating the total ion currents that may be obtained from thermospray ionization of 0.1 M aqueous ammonium acetate, measured as a function of vaporizer temperature and flow rate.

These results correlate well with visual observations. The maximum current corresponds to production of a relatively dry mist in an intense vapor jet; the temperatures corresponding to the maxima in FIG. 5 are in excellent agreement with the optimum temperature vs. flow rate results obtained visually. Also the temperature at which the current vanishes on the high temperature side correlates with disappearance of the mist while the low temperature threshold for current production correlates with the minimum temperature for jet formation. Mass spectra obtained by thermospray ionization of aqueous ammonium acetate show that the positive ion spectra consist almost entirely of $NH_4+$ and its clusters with water, ammonia, and acetic acid while the negative ion spectra consists of the acetate ion clustered with one or two acetic acid molecules.

Figure 6:
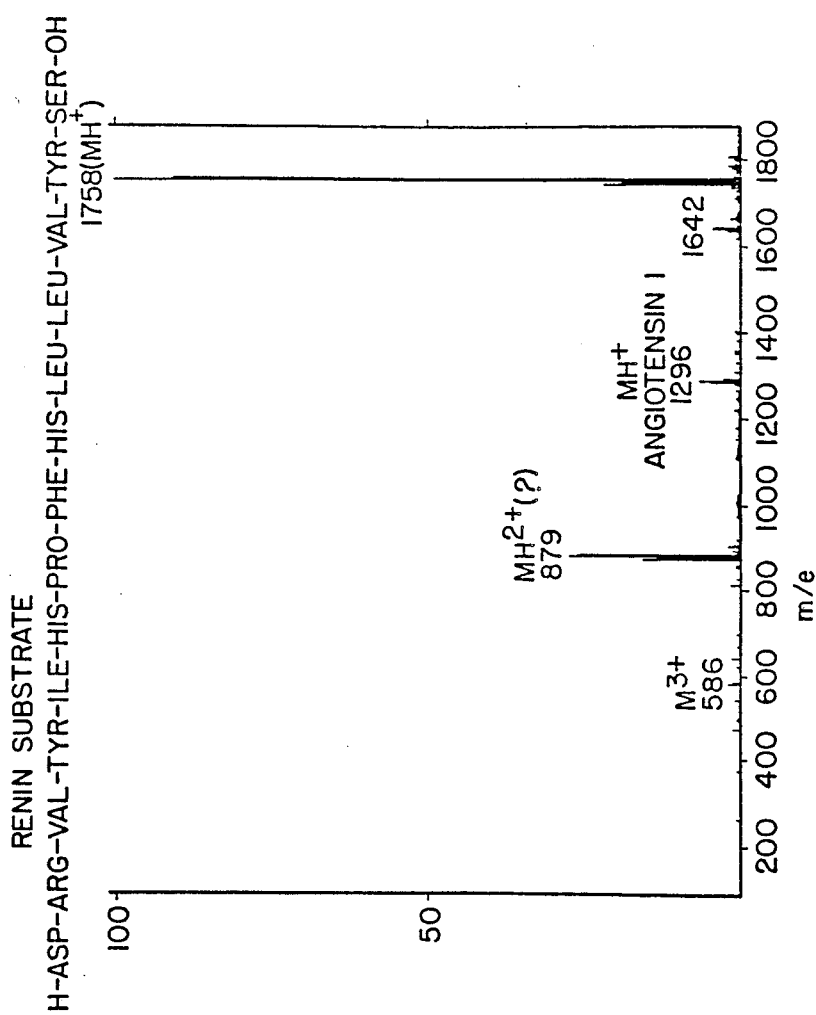
FIG. 6 is a mass spectrum of a tetradecapeptide, renin substrate.
Figure 7:
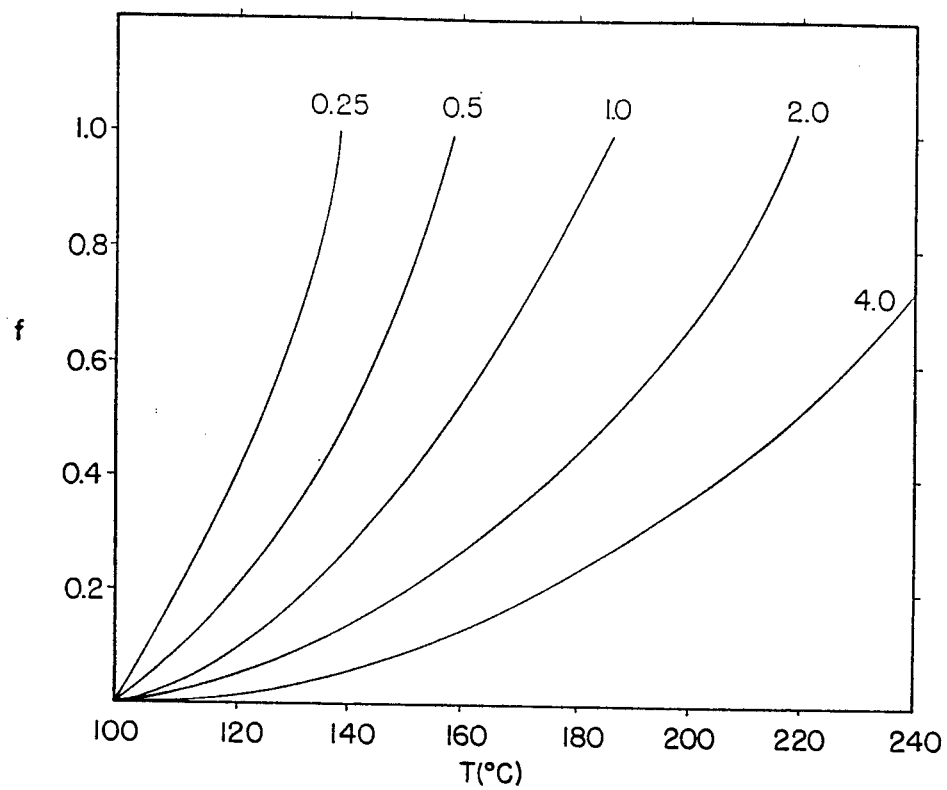
FIG. 7 is a graph illustrating the fraction of water vaporized as the function of exit temperature calculated for an ambient pressure of 1 atm at various flow rates through a 0.15 mm tube.
Figure 8:
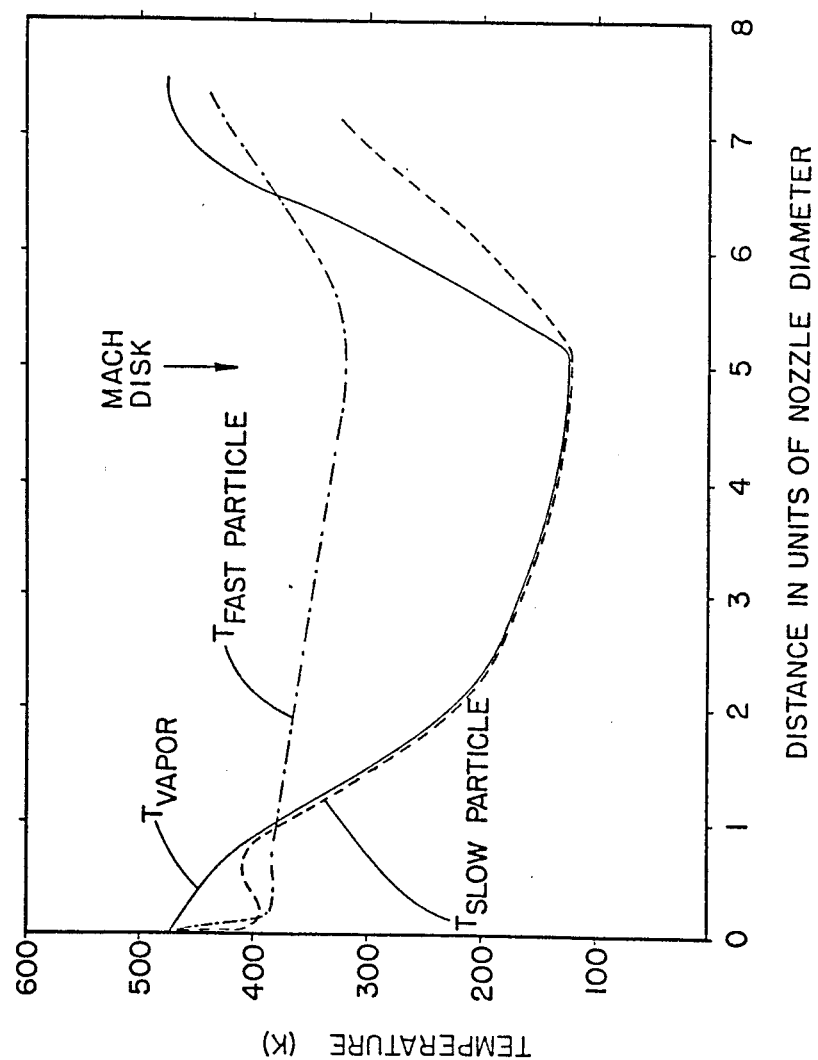
FIG. 8 is a graph illustrating the absolute temperatures as functions of distance downstream from a thermospray vaporizer for vapor, and for fast and slow particles or droplets.

Thermospray ionization appears to provide intact molecular ions for any molecule which is ionized in solution and the efficiency of producing these ions seems nearly independent of the molecular weight and volatility of sample. As an example, a spectrum of the tetradecapeptide renin substrate is shown in FIG. 6. This is one of the largest molecules which has been successfully detected using thermospray ionization to date and is near the upper mass limit of our quadrupole as presently configured. The mass resolution is too low and the mass scale calibration too uncertain in this high mass range to assign with certainty the peaks corresponding approximately to doubly and triply charged ions. From recent results on field desorption of large peptides with multiple ionizable side chains, it is suggested that these are probably doubly and triply protonated molecules. Similar results have been obtained on other molecules with molecular weights in excess of 1000 amu including vitamin $B_{12}$, grammicidin, and several peptides.

Figure 12:
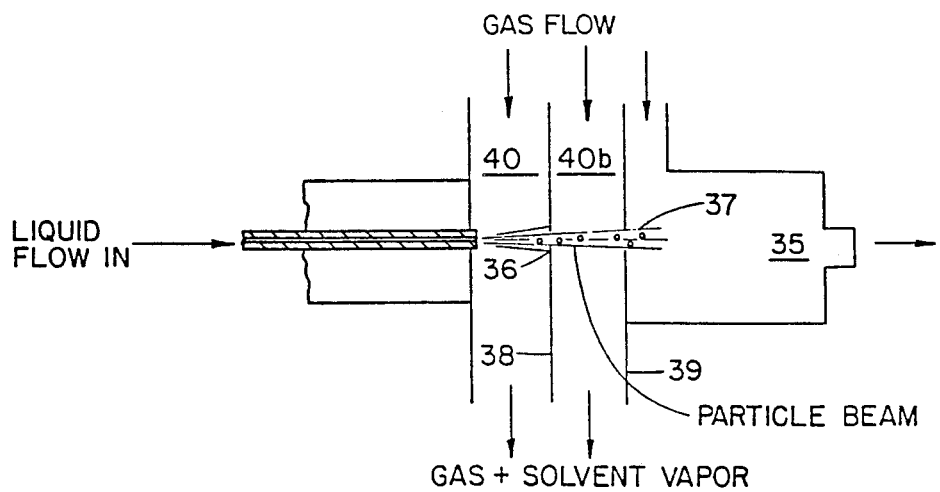
FIG. 12 is a schematic diagram of a gas phase technique for separating sample and solvent utilizing the thermospray apparatus.

We have recently developed a technique for separating the sample from the solvent using thermospray vaporization with a flowing gas system which involves no moving parts and does not require a vacuum system. This concept is illustrated schematically in FIG. 12. In this concept the thermospray jet sprays into a gas stream as illustrated at 40a, 40b (which could be clean air) at atmospheric or higher pressure. The flow of gas is sufficient to sweep away most of the solvent vapor as it is thermalized downstream of the Mach disk, but not so high as to significantly deflect the beam of high velocity particles and droplets generated by the thermospray. The beam of particles passes through a first small aperture 36 into a second region where further separation of solvent vapor and sample particles occur. The gas entering each region may be heated as required to effect additional vaporization of solvent from the droplets or particles. FIG. 12 shows two stages of separation, 40a, 40b, separated by apertured baffles 38 and 39 but depending on the degree of solvent removal required, the number of stages could be reduced to one or increased to as many as is required. At the exit of the solvent separator the particles pass through a final aperture 37 into a suitable detector or analyzer 35. The gas flowing into the detector may be the same as the gas used in the separator or may be different depending on the application.

Figure 13:
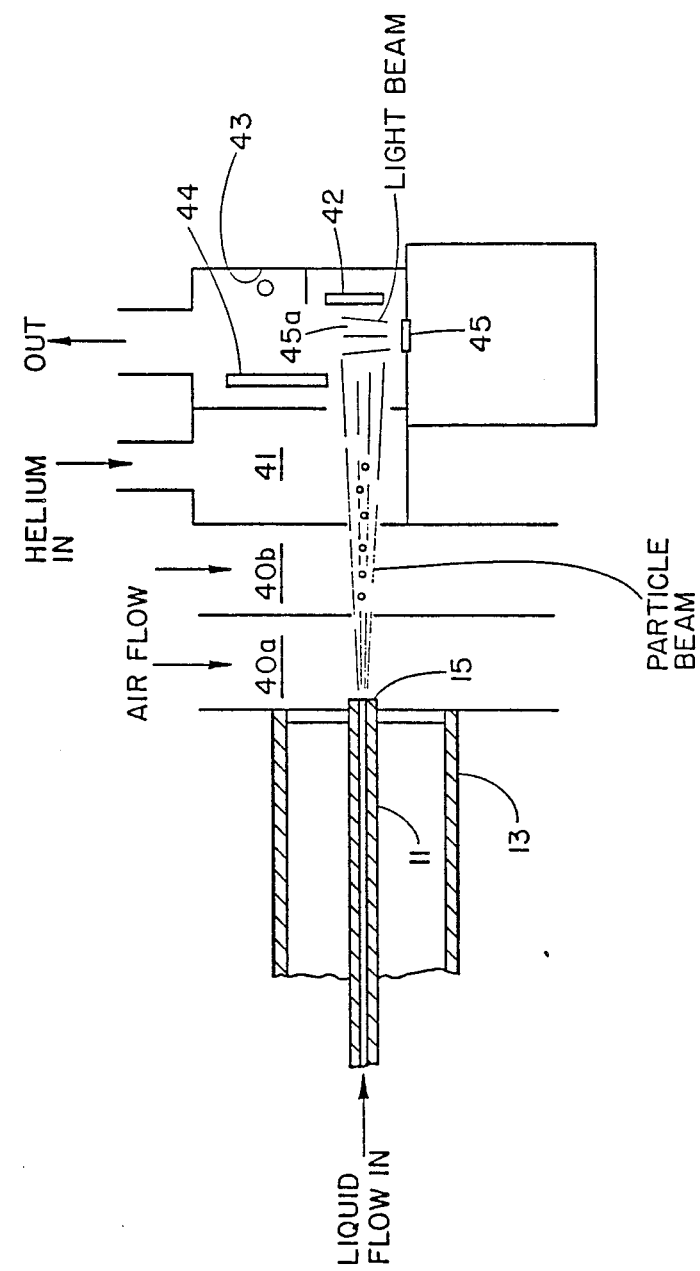
FIG. 13 is a schematic diagram of a UV photoionization detector with thermospray vaporization and gas phase ionization of sample from solvent vapor

An example of the use of this gas phase sample/solvent separator with a photoionization detector is shown in FIG. 13. In this case air is used as the carrier gas in the separation region 40 and helium is used as the flow gas in the detector 41. In most cases small concentrations of air or solvent vapor will not interfere with the photoionization detector, particularly if relatively long wave-length radiation is used. In the version shown in FIG. 13 the particle beam impacts on a heated metal surface 42 where final sample vaporization occurs. Gas phase sample molecules or small clusters are then photoionized and collected at 43. The ion collector may be biased by deflector 44 relative to the hot surface so as to detect ions produced in the gas phase but not those produced directly at the hot surface 42. Alternatively, the collector may be used to monitor ion currents produced directly as the result of particle impact with the heated surface 42 with the UV lamp 45 turned off. Both modes of operation may be of significant utility. In some cases, it may be possible to efficiently vaporize the particles in the beam 45a merely by contact with hot gas in the detector; in this case the heated surface is not required.

Figure 14:
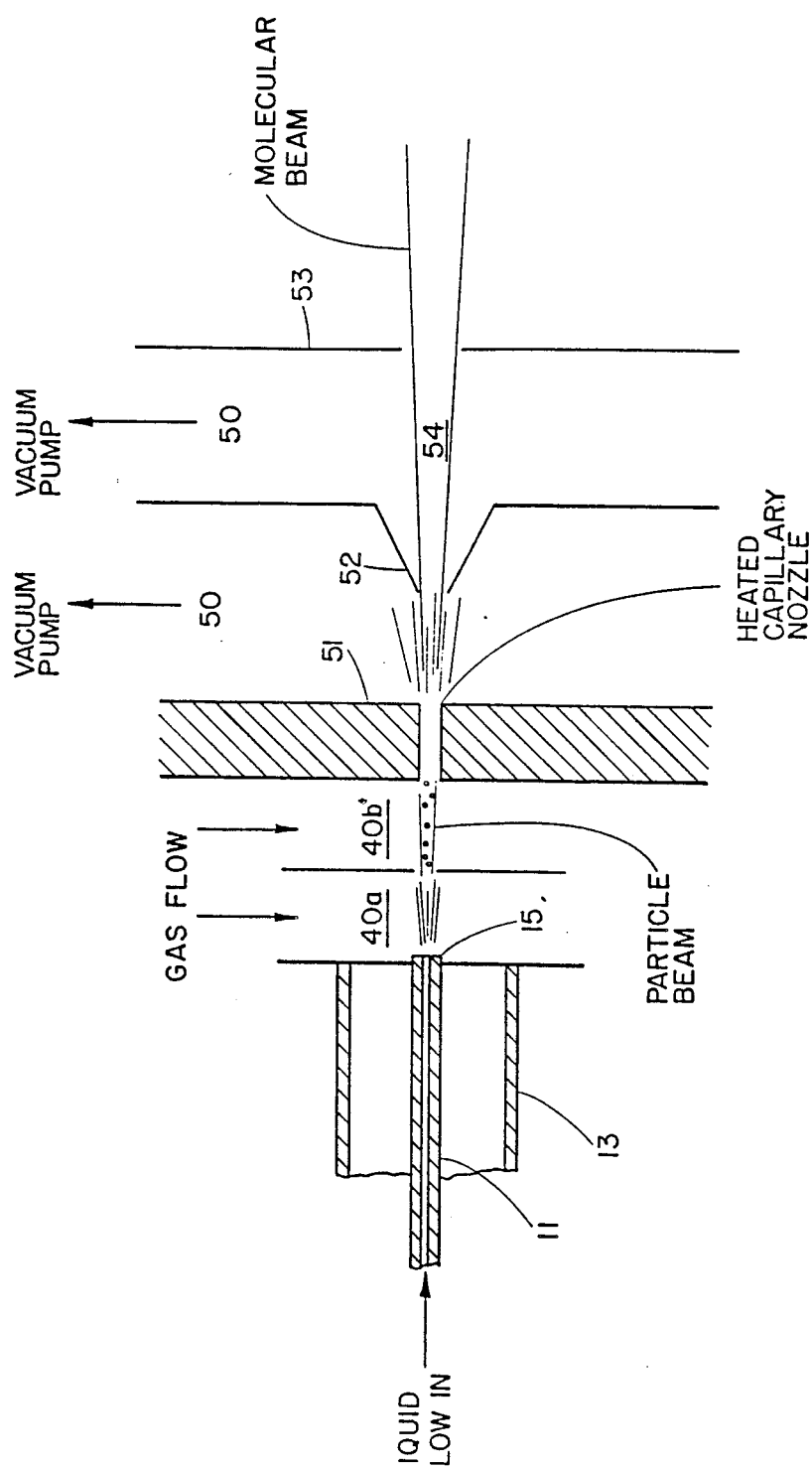
FIG. 14 is a schematic diagram of a thermospray technique for producing supersonic beams of nonvolatile molecules.

The thermospray vaporizer can also be used with gas flow separation of solvent vapor to produce a molecular beam of nonvolatile molecules or small clusters as shown in FIG. 14. If the thermospray jet is directed into a vacuum 50 without solvent removal, the rapid adiabatic cooling will cause recondensation of the vapor onto the particles or droplets. While this technique can probably be used to produce a supersonic particle beam, the particles produced will tend to be rather large and very cold. By using the gas flow separator 40a and 40b it is possible to first separate most of the solvent vapor from the sample particles and then pass the particles through a second heated capillary 51. Downstream of the capillary 51 is a conventional supersonic beam system consisting of a skimmer 52 and collimater 53 with the chambers in between these components separately pumped by large vacuum pumps. As the particles pass through the heated capillary 51 further rapid vaporization can be made to occur resulting in a supersonic "seeded" beam of nonvolatile molecules 54. Depending on the conditions used in the heated capillary 51, it should be possible to achieve either complete or partial vaporization as required.

Figure 11:
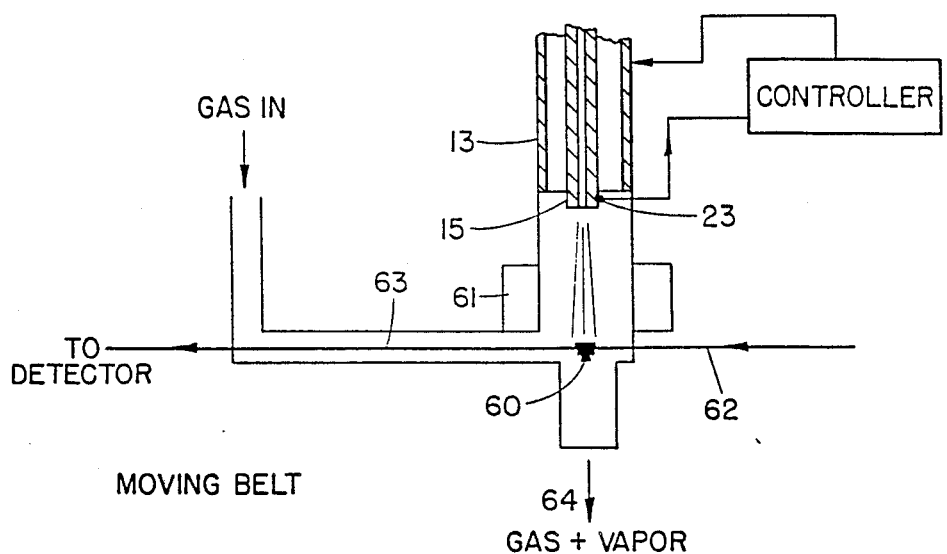
FIG. 11 is a schematic diagram of a means for providing thermospray deposition of non-volatile molecular samples on a moving belt for subsequent detection and/or analysis.

Efficient removal of solvent appears to be quite straightforward by this technique, but maintaining efficient sample transfer requires very close control of both the vaporizer and the downstream environment. For efficient sample transfer it is essential to have the sample contained in the droplets and also have the droplets moving with relatively high velocity. In some cases this may be accomplished simply by proper control of the vaporizer. For example, we have succeeded in obtaining essentially 100% transfer of amino acids in aqueous solution by thermospraying at atmospheric pressure with no control on the downstream environment. On the other hand when operating at lower ambient pressures it appears necessary to confine the vaporization region so that the adiabatic expansion does not continue indefinitely. A schematic diagram of a system for thermospray transfer of samples to a moving belt 62 at atmospheric pressure is shown in FIG. 11. In this system the exit temperature is controlled by feedback control of the vaporizer heater using a temperature sensor 23 attached at or near the end of the capillary 15. The temperature at or near the surface of the belt at the point of jet impact is monitored by a second temperature sensor 60 which controls the input to a heater/cooler 61 attached to the housing surrounding the jet. Depending on the nature of the solvent and sample it may be necessary in some cases to either heat or cool this region to maintain the surface of the belt at an appropriate temperature. This temperature should be low enough that no significant amount of sample is vaporized yet high enough that any residual liquid solvent is vaporized efficiently in a stream of counter-current flowing gas 63 which passes over the belt and exits with the vapor to the exhaust system 64.

The foregoing description of the several embodiments of the thermospray vaporizer and its application is presented for the purpose of illustrating the invention, and is not intended to be exhaustive or to limit the invention to the specific embodiments or means illustrated. They were chosen and described in order to explain the principles of the invention and their practical application to enable those skilled in the art to use the invention. The scope of the invention is to be defined in accordance with the following appended claims.

We claim:

1. A thermospray device for vaporizing a liquid sample into an ion vapor containing large molecules of interest for analysis, said device comprising:
   (a) a metal capillary tube for receiving said sample, said tube defining a nozzle portion at one end thereof,
   (b) heating means for heating said capillary tube to vaporize a predetermined fraction of the sample passing therethrough,
   (c) a control means for controlling the temperature of the sample within the capillary and to maintain from 1% to 35% of the sample in liquid form as it is ejected from the nozzle as a particle beam of minute particles entrained in an intense vapor jet, said control means including a means for measuring the temperature of the liquid sample in the capillary tube, said means for measuring including a temperature sensor mounted in thermal contact with the capillary tube within a first third of a predetermined length heated by said heating means, and
   (d) a means for separating the large molecules from said vapor jet as said molecules are selected for further analysis.

2. The thermospray device as claimed in claim 1 wherein said device comprises an ionization means.

3. The thermospray device as claimed in claim 1 further includes a detecting means for detecting said molecules of interest, said detection means is selected from one of the following:
   (1) photo ionization detection means
   (2) flame ionization detection means
   (3) electron capture detection means
   (4) optical photometry detection means
   (5) atomic absorption detection means, or
   (6) optical admission detection means 4. The thermospray device as claimed in claim 3 wherein said separating means comprises at least one separation chamber in which said vapor jet passes through a gas stream which is flowing perpendicular to said vapor jet in said at least one separation chamber(s), said gas stream being sufficient to sweep away most of the solvent vapor without significantly deflecting said sample molecules.

5. The thermospray device as claimed in claim 4 wherein said separating means comprises a first and second separation chamber having a first baffle with a first aperture which separates said first and second separation chambers, and a second baffle with a second aperture which separates said second separation chamber and said detection means.

6. The thermospray device as claimed in claim 4 wherein said gas stream is clean air.

7. The thermospray device as claimed in claim 4 wherein said gas stream is at atmospheric or higher pressure.

8. The thermospray device as claimed in claim 1 wherein said device further includes a detecting means which comprises a detection chamber in which said molecules from said separating means are deflected by a flow gas to a heated metal surface where final sample vaporization occurs.

9. The thermospray device as claimed in claim 1 wherein said device further includes a detecting means which comprises a detection chamber in which said molecules from said separating means are deflected by a flow gas which is heated to provide final sample vaporization.

10. The thermospray device as claimed in claims 8 or 9 wherein said flow gas is helium.

11. The thermospray device as claimed in claim 1 wherein said separating means comprises a first and second separation chamber in which said vapor jet passes through a gas stream which is flowing perpendicular to said vapor jet in said first and second separation chambers, said gas stream is sufficient to sweep away most of the solvent vapor without significantly deflecting said sample molecules, said separating means includes means for directing said sample molecules through a heated capillary nozzle where further rapid vaporization occurs resulting in a supersonic seeded beam of nonvolatile molecules.

12. The thermospray device as claimed in claim 11 wherein said separating means further comprises a first baffle with a first aperture which separates said first and second separation chambers, and a second baffle with a second aperture which separates said second separation chamber and a vacuum chamber.

13. The thermospray device as claimed in claim 12 wherein said vacuum chamber is a supersonic beam system comprising a skimmer and collimator in which the chambers in between said skimmer and said collimator are separately pumped by a first and second vacuum pump.

14. The thermospray device as claimed in claim 11 wherein said gas stream is at atmospheric or higher pressure.

15. A method of vaporizing a liquid sample containing large molecules of interest for analysis, said method comprising the steps of:

(a) receiving said sample in a metal capillary tube, said tube defining a nozzle portion at one end thereof,
(b) heating said capillary tube to vaporize a predetermined fraction of the sample passing therethrough,
(c) controlling the temperature of the sample within the nozzle and maintaining from 1% to 35% of the sample in liquid form as it is ejected from the nozzle as a particle beam of minute particles entrained in an intense vapor jet, said controlling step includes measuring the temperature of the liquid in the capillary tube, and
(d) separating the large molecules from said vapor jet as said molecules are selected for further analysis.

16. The method of vaporizing a liquid sample according to claim 15 further including a detecting step for detecting said molecules of interest, said detection step is selected from one of the following:
(1) photo ionization detection
(2) flame ionization detection
(3) electron capture detection
(4) optical photometry detection
(5) atomic absorption detection, or
(6) optical admission detection 17. The method of vaporizing a liquid sample according to claim 15 wherein said separating step comprises passing said vapor jet through a first gas stream flowing perpendicular to said vapor jet and subsequently passing said vapor jet through a aperture and through a second gas stream flowing perpendicular to said vapor jet, said first and second gas stream is sufficient to sweep away most of the solvent vapor without significantly deflecting said sample molecules.

18. The method of vaporizing a liquid sample according to claim 15 wherein said detecting and analyzing step comprises deflecting said molecules by a flow gas to a heated metal surface where final sample vaporization occurs, said molecules are then photoionized by an ultra violet lamp and collected for analysis.

19. The method of vaporizing a liquid sample according to claim 15 wherein said detecting and analyzing step comprises deflecting said molecules by a heated flow gas causing final sample vaporization, said molecules are then photoionized by an ultra violet lamp and collected for analysis.

20. The method of vaporizing a liquid sample according to claim 15 wherein said separating step comprises passing said vapor jet through a first and second gas stream flowing perpendicular to said vapor jet and sweeping away most of the solvent vapor without significantly deflecting said sample molecules and subsequently passing the molecules through a heated c capillary nozzle where further rapid vaporization occurs resulting in a supersonic seeded beam of nonvolatile molecules.

21. The method of vaporizing a liquid sample according to claim 20 wherein said separating step further comprises passing said supersonic beam through a vacuum chamber for adiabatic cooling.

* * * * *

UNITED STATES PATENT AND TRADEMARK OFFICE
CERTIFICATE OF CORRECTION

PATENT NO. : 4,960,992

DATED : October 2, 1990

INVENTOR(S) : Marvin Vestal, et al.

It is certified that error appears in the above-identified patent and that said Letters Patent is hereby corrected as shown below:

In the Drawings, Sheet 12 of 20: "IQUID LOW IN" should read as --LIQUID FLOW IN--

Column 2, line 21: "use-a" should read as --use a--

Column 3, line 4: "capillary" should read as --capillary.--

Column 3, line 39: "solution" should read as --solution.--

Column 4, line 3: "surface" should read as --surface.--

Column 4, lines 4-5: "spectrometer methods" should read as --spectrometer. Methods--

Column 4, line 19: "nonvolatile.," should read as --nonvolatile,--

Column 5, line 47: "block" should read as --block.--

Column 5, line 53: "fluid" should read as --fluid.--

Column 6, line 2: "capillary" should read as --capillary.--

Column 7, Line 8: "be," should read as --be--

Column 8, line 3: "vapor" should read as --vapor.--

Column 10, line 15: "exhausted" should read as --exhausted.--

Column 10, line 19: "28" should read as --28.--

UNITED STATES PATENT AND TRADEMARK OFFICE
CERTIFICATE OF CORRECTION

PATENT NO. : 4,960,992

DATED : October 2, 1990

INVENTOR(S) : Marvin Vestal, et al.

It is certified that error appears in the above-identified patent and that said Letters Patent is hereby corrected as shown below:

Column 10, line 27: "a . capillary" should read as --a capillary--

Column 10, line 30: "systems" should read as --systems.--

Column 10, line 51: "cf" should read as --of--

Column 10, line 56: "heater supply" should read as --heater power supply--

Column 12, line 44: "$T_1$ as" should read as --$T_1$ constant as--

Column 13, line 24: "$\Delta H_v/CL$" should read as --$\Delta H_v/C_L$--

Column 13, line 32: "$\Delta H_v$ depends" should read as --$\Delta H_v$ depends--

Column 13, line 67: "p3" should read as --$p_e$--

Column 14, line 52: "$L/L_1=6$" should read as --$L/L_1 = 6$--

Column 16, line 29: "sensitivities" should read as --sensitivities.--

Column 16, line 59: "$x_o$ 32 0.6d," should read as --$x_o = 0.6d$,--

Column 16, line 60: "and = is" should read as --and x is--

Column 17, line 26: "enthalpy" should read as --enthalpy.--

UNITED STATES PATENT AND TRADEMARK OFFICE
CERTIFICATE OF CORRECTION

PATENT NO. : 4,960,992

DATED : October 2, 1990

INVENTOR(S) : Marvin Vestal, et al.

It is certified that error appears in the above-identified patent and that said Letters Patent is hereby corrected as shown below:

Column 19, line 17: delete ","

Column 20, line 31: "vaporizers While" should read as --vaporizers. While--

Column 21, line 48: "surfaces-is" should read as --surfaces is--

Column 21, line 51: "neutrals It" should read as --neutrals. It--

Column 23, line 11: "FIG. 13" should read as --FIG. 3--

Column 26, line 52, Claim 20: delete "c"

Signed and Sealed this

Eighteenth Day of August, 1992

Attest:

DOUGLAS B. COMER

Attesting Officer

Acting Commissioner of Patents and Trademarks